US011137406B2

(12) United States Patent
Tamura et al.

(10) Patent No.: US 11,137,406 B2
(45) Date of Patent: Oct. 5, 2021

(54) METHOD FOR DISCRIMINATING MICROORGANISM

(71) Applicants: SHIMADZU CORPORATION, Kyoto (JP); MEIJO UNIVERSITY, Nagoya (JP)

(72) Inventors: Hiroto Tamura, Nagoya (JP); Naomi Yamamoto, Nagoya (JP); Teruyo Kato, Toyota (JP); Keisuke Shima, Kyoto (JP); Shinji Funatsu, Kyoto (JP)

(73) Assignees: SHIMADZU CORPORATION, Kyoto (JP); MEIJO UNIVERSITY, Nagoya (JP)

(*) Notice: Subject to any disclaimer, the term of this patent is extended or adjusted under 35 U.S.C. 154(b) by 152 days.

(21) Appl. No.: 16/089,828

(22) PCT Filed: Mar. 31, 2016

(86) PCT No.: PCT/JP2016/060867
§ 371 (c)(1),
(2) Date: Sep. 28, 2018

(87) PCT Pub. No.: WO2017/168742
PCT Pub. Date: Oct. 5, 2017

(65) Prior Publication Data
US 2019/0242903 A1    Aug. 8, 2019

(51) Int. Cl.
*G01N 33/68* (2006.01)
*C12Q 1/04* (2006.01)
(Continued)

(52) U.S. Cl.
CPC ........... *G01N 33/6851* (2013.01); *C12Q 1/04* (2013.01); *G16B 10/00* (2019.02); *G16B 45/00* (2019.02); *Y02A 50/30* (2018.01)

(58) Field of Classification Search
None
See application file for complete search history.

(56) References Cited

U.S. PATENT DOCUMENTS

2004/0234952 A1    11/2004  Kallow et al.
2012/0264156 A1    10/2012  Beaulieu et al.
(Continued)

FOREIGN PATENT DOCUMENTS

CN    102656276 A    9/2012
CN    104797939 A    7/2015
(Continued)

OTHER PUBLICATIONS

Paauw, A. et al. Rapid and reliable discrimination between Shigella species and *Escherichia coli* using MALDI-TOF mass spectrometry, International Journal of Medical Microbiology, 305 (2015) 446-452 (Year: 2015).*

(Continued)

*Primary Examiner* — Xiaoyun R Xu
(74) *Attorney, Agent, or Firm* — Sughrue Mion, PLLC

(57) ABSTRACT

To provide a method for discriminating a microorganism including: a step of subjecting a sample containing a microorganism to mass spectrometry to obtain a mass spectrum; a reading step of reading a mass-to-charge ratio m/z of a peak derived from a marker protein from the mass spectrum; and a discrimination step of discriminating which bacterial species of *Escherichia coli*, *Shigella* bacteria, and *Escherichia albertii* the microorganism contained in the sample contains based on the mass-to-charge ratio m/z, in which at least one of 13 ribosomal proteins S5, L15, S13, L31, L22, L19, L20, L13, S15, L25, HNS, HdeB, and L29 is used as the marker protein.

4 Claims, 25 Drawing Sheets

(51) Int. Cl.
G16B 10/00 (2019.01)
G16B 45/00 (2019.01)

(56) References Cited

U.S. PATENT DOCUMENTS

2014/0051113 A1 2/2014 Stephenson, Jr. et al.
2014/0288852 A1 9/2014 Ojima et al.

FOREIGN PATENT DOCUMENTS

| EP | 1437673 A1 | 7/2004 |
| EP | 2488660 A2 | 8/2012 |
| EP | 2845011 A1 | 3/2015 |
| JP | 2006191922 A | 7/2006 |
| JP | 2013508675 A | 3/2013 |
| JP | 2013085517 A | 5/2013 |
| JP | 2015521035 A | 7/2015 |
| JP | 2015184020 A | 10/2015 |
| KR | 1020120102634 A | 9/2012 |
| WO | 2011045544 A2 | 4/2011 |
| WO | 2013166169 A1 | 11/2013 |

OTHER PUBLICATIONS

Bilecen, K. et al. Performances and Reliability of Bruker Microflex LT and VITEK MS MALDI-TOF Mass Spectrometry Systems for the Identification of Clinical Microorganisms, BioMed Research International, vol. 2015, Article ID 516410, 18 pages (Year: 2015).*
The Extended European Search Report dated Nov. 26, 2019, issued by the European Patent Office in application No. 16896959.0.
Teruyo Ojima-Kato et al., "Discrimination of *Escherichia coli* O157, O26 and O111 from Other Serovars by MALDI-TOF MS Based on the S10-GERMS Method", PLOS ONE, Nov. 2014, vol. 9, Issue 11, e113458, pp. 1-11.
Teruyo Ojima-Kato et al., "Assessing the performance of novel software Strain Solution on automated discrimination of *Escherichia coli* serotypes and their mixtures using matrix-assisted laser desorption ionization-time of flight mass spectrometry", Journal of Microbiological Methods, 2015, vol. 119, pp. 233-238.
Brenner, D.J., et al. " Polynucleotide Sequence Relatedness Among *Shigella* Species", International Journal of Systematic Bacteriology, vol. 23, No. 1, (7 pages).
Manual for Test and Diagnosis of Shigella—National Institute of Infectious Disease, 2016, pp. 1-17, (17 pages), www.nih.go.jp/niid/images/lab-manual/shigella.
Comprehensive Survey of Ensuing Food Safety 2010, "Report on Literature Review on Infections Mediated by Food (excerpt)", prepared by Toray Research Center, Inc., 2016, 24 pages, https://www.fsc.go.jp/sonota/hazard/H22_10.
Huys, G., et al., "*Escherichia albertii* sp. nov., a diarrhoeagenic species isolated from stool specimens of Bangladeshi children", International Journal of Systematic and Evolutionary Microbiology, 2003, vol. 53, No. 3, pp. 807-810 (4 pages).
Ooka, T., et al., "Clinical Significance of *Eschericia albertii*", Emerging Infectious Diseases, 2012, vol. 18, No. 3, pp. 488-492 (5 pages).
Hyma, K., et al., "Evolutionary Genetics of a New Pathogenic *Escherichia* Species: *Escherichia albertii* and Related *Shigella boydii* Strains", Journal of Bacteriology, 2005, vol. 187, No. 2, pp. 619-628 (10 pages).
Murakami, K., et al., "Shiga Toxin 2f-Producing *Escherichia albertii* from a Symptomatic Human", Japanese journal of infectious diseases, 2014, vol. 67, No. 3, pp. 204-208 (5 pages).

Watanabe, H., et al., " Genetic Analysis of an Invasion Region by Use of a Tn3-lac Transposon and Identification of a Second Positive Regulator Gene, invE, for Cell Invasion of *Shigella sonnei*: Significant Homology of InvE with ParB of Plasmid P1", Journal of Bacteriology, 1990, vol. 172, No. 2, pp. 619-629 (11 pages).
Thiem, V-D., et al., "Detection of *Shigella* by a PCR Assay Targeting the ipaH Gene Suggests Increased Prevalence of Shigellosis in Nha Trang, Vietnam", Journal of Clinical Microbiology, 2004, vol. 42, No. 5, pp. 2031-2035 (5 pages).
Lukjancenko, O., et al., "Comparison of 61 Sequenced *Escherichia coli* Genomes", Microbial ecology, 2010, vol. 60, No. 4, pp. 708-720 (13 pages).
Hotta, Y., et al., "Classification of the Genus *Bacillus* Based on MALDI-TOF MS Analysis of Ribosomal Proteins Coded in S10 and spc Operons", Journal of Agricultural and Food Chemistry, 2011, vol. 59, pp. 5222-5230 (9 pages).
Suarez, S., et al., "Ribosomal proteins as biomarkers for bacterial identification by mass spectrometry in the clinical microbiology laboratory", Journal of Microbiological Methods, 2013, vol. 94, pp. 390-396 (7 pages).
Rasko, D., et al., "The Pangenome Structure of *Escherichia coli*: Comparative Genomic Analysis of *E. coli* Commensal and Pathogenic Isolates", Journal of Bacteriology, 2008, vol. 190, No. 20, pp. 6881-6893 (13 pages ).
Oaks, J., et al., "*Escherichia albertii* in Wild and Domestic Birds", Emerging Infectious Diseases, 2010, vol. 16, No. 4, pp. 638-646 (9 pages).
Dallagassa, C.B., et al., "Matrix-assisted laser desorption ionization-time of flight mass spectrometry analysis of *Escherichia coli* categories", Genetics and Molecular Research, 2014, vol. 13., No. 1, pp. 716-722 (7 pages).
Deng, J., et al., "Comparison of MALDI-TOF MS, gene sequencing and the Vitek 2 for identification of seventy-three clinical isolates of enteropathogens", Journal of thoracic disease, 2014, Journal of Thoracic Disease, vol. 6, No. 5, pp. 539-544 (6 pages).
Khot, P., et al., "Novel Approach for Differentiating *Shigella* Species and *Escherichia coli* by Matrix-Assisted Laser Desorption Ionization-Time of Flight Mass Spectrometry", Journal of Clinical Microbiology, 2013, vol. 51, No. 11, pp. 3711-3716 (6 pages).
Mott, T., et al., "Comparison of MALDI-TOF/MS and LC-QTOF/MS methods for the identification of enteric bacteria", International Journal of Mass Spectrometry, 2010, vol. 291, pp. 24-32 (9 pages).
Holland, R., et al., "Identification of Bacterial Proteins Observed in MALDI TOF Mass Spectra from Whole Cells", Analytical Chemistry, 1999, vol. 71, No. 15, pp. 3226-3230 (5 pages).
Konno, T., et al., "Shokuchudoku Utagai Jirei Kensa ni Okeru Shinki Byogenkin *Escherichia albertii* no Kenshuthu", Akita-Ken Kenko Kankyo Center Nenpo, 2011, No. 7, pp. 63-66 (5 pages).
Teramoto, K., et al., "Rapid Classification and Identification of Bacteria by Matrix-Assisted Laser Desorption/Ionization-Mass Spectrometry Using Ribosomal Proteins as Biomarkers", Journal of the Mass Spectrometry Society of Japan, 2007, vol. 55, No. 3, pp. 209-216 (8 pages).
Teramoto, K., " Classification and Identification of Bacteria by Matrix-Assisted Laser Desorption/Ionization-Mass Spectrometry Using Ribosomal Protein as Biomarkers", Journal of the Mass Spectrometry Society of Japan, 2011, Vo. 59, No. 5, pp. 85-94 (10 pages).
International Preliminary Report on Patentability and Translation of Written Opinion, dated Oct. 2, 2018 from the International Bureau in counterpart International application No. PCT/JP2016/060867.

* cited by examiner

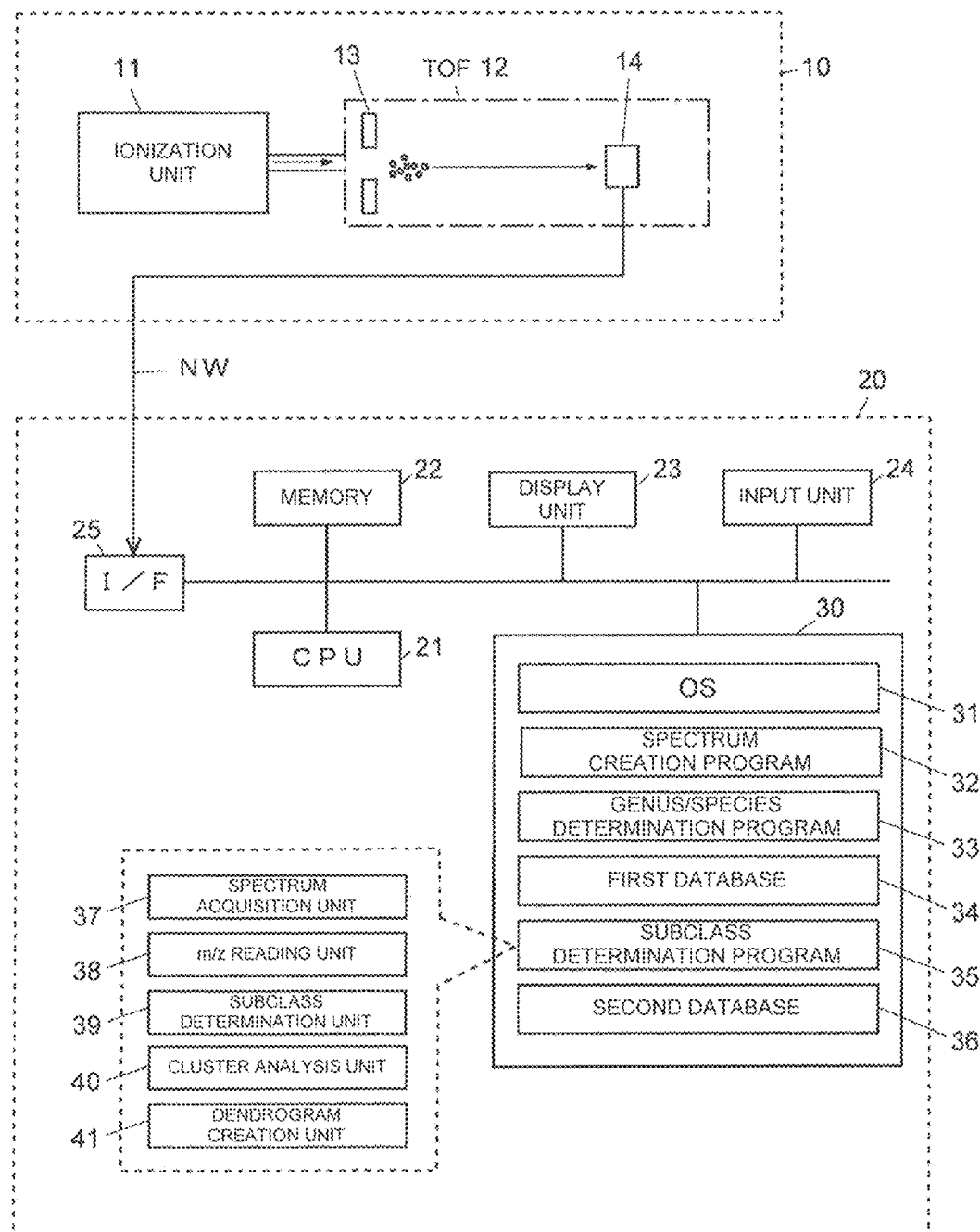

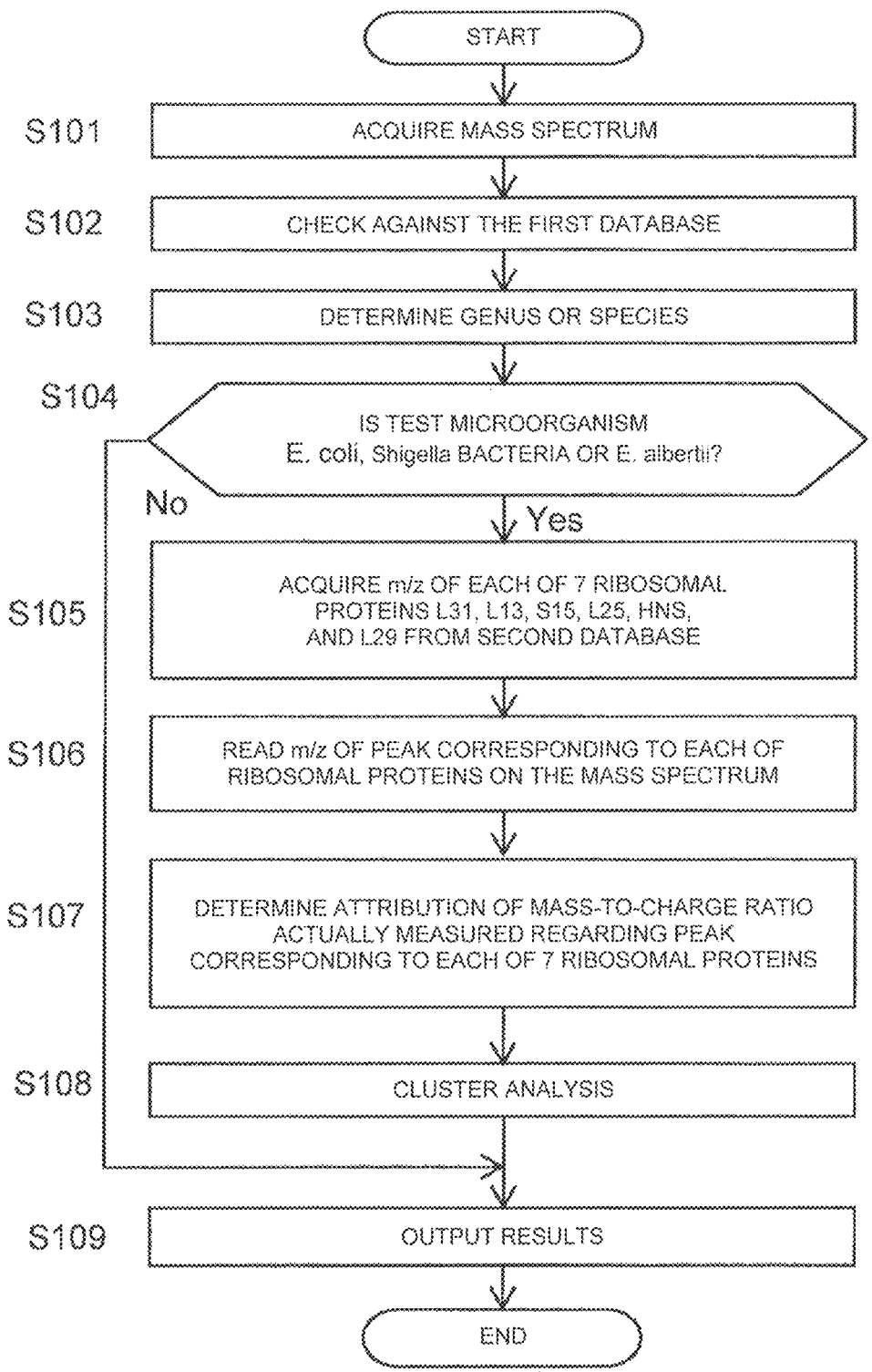

Fig. 3

| No. | Genus | Species | Strain | serovar(Penner) | Supplier |
|---|---|---|---|---|---|
| 1 Ea1 | Escherichia | albertii | JCM17328T | | JCM |
| 2 B133 | Escherichia | coli | NBRC12713 | | NBRC |
| 3 Shi1 | Shigella | dysenteriae | GTC00786T | | NBRP(GTC) |
| 4 Shi2 | Shigella | flexneri | GTC00780T | serotype2a | NBRP(GTC) |
| 5 Shi3 | Shigella | sonnei | GTC00781T | | NBRP(GTC) |
| 7 Shi5 | Shigella | boydii | GTC00779T | | NBRP(GTC) |
| 11 Ec13 | Escherichia | coli | GTC14546 | O157:H7 | NBRP(GTC) |
| 12 Ec15 | Escherichia | coli | GTC14550 | O157:H7 | NBRP(GTC) |
| 13 Ec2 | Escherichia | coli | GTC14507 | O111:H- | NBRP(GTC) |
| 14 Ec10 | Escherichia | coli | GTC14538 | O26:H- | NBRP(GTC) |

NBRC: Biological Resource Center, NITE
JCM: Riken Japan Collection of Microorganisms
NBRP (GTC): Gifu University School of Medicine

Fig. 4

| Name | Sequence (5' – 3') | Purpose |
|---|---|---|
| EcW3110-S10-F | AAGAACGGTTACACTCTCCC | amplification of *S10* region |
| EcW3110-S10-R | ACACCGCTTCAAGGATATGG | amplification of *S10* region |
| EcW3110-S10-1 | AATCGTAATGGGTCTGAGGAG | sequencing |
| EcW3110-S10-2 | AAGCTGGCCACTTCGCTAAAG | sequencing |
| EcW3110-S10-3 | TGCTGAAGTAACTGGTTCCGG | sequencing |
| EcW3110-S10-4 | AAGCTGCTGTGCAGAAACTG | sequencing |
| EcW3110-S10-5 | CATAACGTAGAAATGAAACCAGG | sequencing |
| EcW3110-S10-6 | ACGTTCCGGTATTTGTAACCG | sequencing |
| EcW3110-S10-7 | TCAGTACCTGACTAAGGAAC | sequencing |
| EcW3110-S10-8 | AGCGTCGCTGATGTTACAAC | sequencing |
| EcW3110-S10-9 | AGCAAGTGCGTCGCGATGTCG | sequencing |
| EcW3110-S10-10 | GCTGGCATGATTCGTGAAGAACG | sequencing |
| EcW3110-spc-F | AACGGCTCAGAAATGAGCCG | amplification of *spc* region |
| EcW3110-spc-R | AGCAGTCTGCGTTCAGCTC | amplification of *spc* region |
| EcW3110-spc-1 | TCTACCCATATCCTTGAAGC | sequencing |
| EcW3110-spc-2 | ATTGTTGAAGGTATCAACCTG | sequencing |
| EcW3110-spc-3 | TCGTGGTAACTACAGCATG | sequencing |
| EcW3110-spc-4 | ACCATGCCTTCCTCCAAGCT | sequencing |
| EcW3110-spc-5 | TTGGTGTAGGTTACCGTGCAG | sequencing |
| EcW3110-spc-6 | ATGCTGCCCGTGAAGCTGGC | sequencing |
| EcW3110-spc-7 | ATCGGTCGTCTGCCGAAACAC | sequencing |
| EcW3110-spc-9 | GTCACCATGCCTTCCTCCAAG | sequencing |
| EcW3110-spc-1r | GATGATGTCGCCTACGCCTGC | sequencing |
| EcW3110-spc-2r | TTACCGGTTAACACGATAAC | sequencing |
| EcW3110-alpha-F | AGTGCCAAAGGTGGCTTACGC | amplification of *alpha* region |
| EcW3110-alpha-R | ACAGCTATTGTAGATAAGTGG | amplification of *alpha* region |
| EcW3110-alpha-1 | TGCCCATACTATCGAGCAAGC | sequencing |
| EcW3110-alpha-2 | TCACTGCTTATCGTTGTTGTC | sequencing |
| EcW3110-alpha-3 | TGTCGTTGAAGGTGATCTGCG | sequencing |
| EcW3110-alpha-4 | AATGGCAAGATATTTGGGTC | sequencing |
| EcW3110-alpha-5 | TGCGGACATTAACGAACACCTG | sequencing |
| EcW3110-alpha-6 | TGCCTACAATGTTGAAGCAGCG | sequencing |
| EcW3110-alpha-7 | AGCTGCGCCGCGTAGTTGAGC | sequencing |
| EcW3110-alpha-1r | AGCTGGATAATGATCGACGC | sequencing |
| EcW3110-L25-F | TTCGAGCAGCTTTTATCCGCC | amplification of L25 |
| EcW3110-L25-R | AAGGCTACGAACTGGAAGAGAGC | amplification of L25 |
| EcW3110-L25-1 | ATACGCGCACACCGGGCATC | sequencing |
| EcW3110-L25-1r | AGACCGTAGCACACTGCGTCAG | sequencing |
| EcW3110-S15-F | TACGAACGATCGGATTAAGCAATG | amplification of S15 |
| EcW3110-S15-R | TTACTTGATCCATTACTGATGCC | amplification of S15 |
| EcW3110-S15-1 | GGATTAAGCAATGTAATATCC | sequencing |
| EcW3110-S15-1r | ATTACTGATGCCAATGGACAGTCC | sequencing |
| Ec_HdeB-F | GATATGTAATTCCGGGAATGC | amplification and sequencing of HdeB |
| Ec_HdeB-R | AAGGAGCAGCAAGATGGCTCAAC | amplification of HdeB |
| Ec_HNS-F | TGAATTCCTTACATTCCTGGC | amplification and sequencing of H-NS |
| Ec_HNS-R | AGCTTATTCTTATTAAATTGTC | amplification of H-NS |

Fig. 5

| amino acid | mass |
|---|---|
| A | 71.079 |
| R | 156.188 |
| N | 114.103 |
| D | 115.088 |
| C | 103.145 |
| Q | 128.13 |
| E | 129.114 |
| G | 57.052 |
| H | 137.141 |
| I | 113.159 |
| L | 113.159 |
| K | 128.174 |
| M | 131.198 |
| F | 147.176 |
| P | 97.116 |
| S | 87.078 |
| T | 101.104 |
| W | 186.213 |
| Y | 163.175 |
| V | 99.132 |

Fig. 6A

| Strain \ Protein name | S15 | L25 | HdeB | HNS | L19 | L20 | L29 | |
|---|---|---|---|---|---|---|---|---|
| Ec_K12_W3110 | 10138.57 | 1 | 10694.43 | 1 | 9066.24 | 1 | 15409.42 | 1 | 13003.02 | 1 | 13366.76 | 1 | 7274.44 | 1 |
| Ea_JCM17328T | 10138.57 | 1 | 10593.37 | 4 | 9049.30 | 2 | 15427.41 | 2 | 13017.05 | 2 | 13384.80 | 2 | 7261.45 | 1-2 |
| Shigella_dysenteriae_GTC00786 | 10138.57 | 1 | 10694.43 | 1 | 9048.20 | 3 | 15409.42 | 1 | 13003.02 | 1 | 13396.78 | 3 | 7302.50 | 1-4 |
| Shigella_flexneri_GTC00780 | 10126.57 | 1 | 10694.43 | 1 | 9066.24 | 1 | 15409.42 | 1 | 13003.02 | 1 | 13366.78 | 1 | 7288.47 | 1-3 |
| Shigella_sonnei_GTC00781 | 10138.57 | 1 | 10694.43 | 1 | 9066.24 | 1 | 15409.42 | 1 | 13003.02 | 1 | 13366.76 | 1 | 7274.44 | 1 |
| Shigella_boydii_GTC00779 | 10138.57 | 1 | 10694.43 | 3 | 9066.24 | 1 | 15437.43 | 3 | 13003.02 | 1 | 13366.76 | 1 | 7274.44 | 1 |
| Ec_O157-1_GTC14546-13 | 10168.62 | 2 | 10676.39 | 2 | ND | 0 | 15409.42 | 1 | 13003.02 | 1 | 13366.76 | 1 | 7274.44 | 1 |
| Ec_O157-2_GTC14550-15 | 10138.57 | 1 | 10694.43 | 1 | ND | 0 | 15409.42 | 1 | 13003.02 | 1 | 13366.76 | 1 | 7274.44 | 1 |
| Ec_O111_GTC14507-2 | 10138.57 | 1 | 10694.43 | 1 | 9066.24 | 1 | 15427.41 | 2 | 13003.02 | 2 | 13366.76 | 1 | 7274.44 | 1 |
| Ec_O26_GTC14539-14 | 10138.57 | 1 | 10694.43 | 1 | 9066.24 | 1 | 15427.41 | 2 | 13003.02 | 1 | 13366.76 | 1 | 7274.44 | 1 |
| Actual Measurement | ○ | | ○ | | ○ | | ○ | | ○ | | △ | | ○ | |

| | L31 | S05 | S13 | L13 | S10 | L15 | L22 | |
|---|---|---|---|---|---|---|---|---|
| | 7872.08 | 1 | 17473.18 | 1 | 12969.20 | 1 | 16019.52 | 1 | 11736.57 | 1 | 14981.41 | 1 | 12227.29 | 1 |
| | 7886.11 | 2 | 17473.18 | 1 | 12963.22 | 2 | 16019.52 | 2 | 11736.57 | 1 | 14961.41 | 1 | 12227.29 | 1 |
| | 7872.08 | 1 | 17445.13 | 2 | 12969.20 | 1 | 15959.42 | 4 | 11736.57 | 1 | 14967.38 | 2 | 12227.29 | 1 |
| | 7854.04 | 3 | 17473.18 | 1 | 12969.20 | 1 | 16019.52 | 1 | 11736.57 | 1 | 14967.38 | 2 | 12242.28 | 2 |
| | 7872.08 | 1 | 17473.18 | 1 | 12969.20 | 1 | 16003.55 | 2 | 11736.57 | 1 | 14967.38 | 2 | 12227.29 | 1 |
| | 7872.08 | 1 | 17473.18 | 1 | 12969.20 | 1 | 15966.48 | 3 | 11736.57 | 1 | 14981.41 | 2 | 12227.29 | 1 |
| | 7872.08 | 1 | 17473.18 | 1 | 12969.20 | 1 | 16019.52 | 1 | 11736.57 | 1 | 14981.41 | 1 | 12227.29 | 1 |
| | 7872.08 | 1 | 17473.18 | 1 | 12969.20 | 1 | 16019.52 | 1 | 11736.57 | 1 | 14981.41 | 1 | 12227.29 | 1 |
| | 7872.08 | 1 | 17473.18 | 1 | 12969.20 | 1 | 16019.52 | 1 | 11736.57 | 1 | 14981.41 | 1 | 12227.29 | 1 |
| | 7872.08 | 1 | 17473.18 | 1 | 12969.20 | 1 | 16019.52 | 1 | 11736.57 | 1 | 14981.41 | 1 | 12227.29 | 1 |
| | ○ | | ○ | | ○ | | ○ | | ○ | | △ | | △ | |

Fig. 6B

| AttributionNo | S15 | L25 | HdeB | HMS | L19 | L20 | L29 | L31 | S05 | S13 | L13 | S10 | L15 | L22 |
|---|---|---|---|---|---|---|---|---|---|---|---|---|---|---|
| 1 | 10138.57 | 10694.42 | 9066.24 | 15409.42 | 13003.02 | 13386.76 | 7274.44 | 7672.08 | 17473.18 | 12963.20 | 16019.52 | 11736.57 | 14981.41 | 12227.29 |
| 2 | 10166.62 | 10676.29 | 9049.20 | 15427.41 | 13017.03 | 13384.80 | 7261.45 | 7666.11 | 17445.13 | 12983.22 | 16033.55 | | 14967.39 | 12242.26 |
| 3 | | 10664.41 | 9048.20 | 15437.43 | | 13296.78 | 7268.47 | 7654.04 | | | 15986.49 | | | |
| 4 | | 10593.37 | | | | | 7302.50 | | | | 15959.42 | | | |

Fig. 7A

| Strain\Protein name | L31 | HdeB | S10 | L22 | S15 | L25 | HNS | L19 | L20 | L29 | S05 | S13 | L13 | L15 |
|---|---|---|---|---|---|---|---|---|---|---|---|---|---|---|
| Ec_K12 W3110 | 1 | 1 | 1 | 1 | 1 | | | 1 | | | 1 | 1 | 1 | 1 |
| Ea_JCM17329T | 2 | 2 | 1 | 1 | 1 | 4 | 2 | 2 | 2 | 1-2 | 1 | 2 | 1 | 1 |
| Shigella_dysenteriae_GTC00786T | 1 | 3 | 1 | 1 | 1 | 1 | 1 | 1 | 3 | 1-4 | 2 | 1 | 4 | 2 |
| Shigella_flexneri_GTC00780T | 3 | 1 | 1 | 2 | 1 | 1 | 1 | 1 | 3 | 1-3 | | 1 | 1 | 2 |
| Shigella_sonnei_GTC00781T | 1 | 1 | 1 | 1 | 1 | 1 | 1 | 1 | 1 | 1 | 1 | 1 | 2 | 2 |
| Shigella_boydii_GTC00779T | 1 | 1 | 1 | 1 | 1 | 3 | 3 | 1 | 1 | 1 | 1 | 1 | 3 | 2 |
| Ec_O157-1_GTC14546-13 | 1 | 0 | 1 | 1 | 2 | 2 | | 1 | 1 | 1 | 1 | 1 | 1 | 2 |
| Ec_O157-2_GTC14550-15 | 1 | 0 | 1 | 1 | 1 | 1 | | 1 | 1 | 1 | 1 | 1 | 1 | 2 |
| Ec_O111_GTC14507-2 | 1 | 1 | 1 | 1 | 1 | 1 | 2 | 1 | 1 | 1 | 1 | 1 | 1 | 2 |
| Ec_O26_GTC14528-18 | 1 | 1 | 1 | 1 | 1 | 1 | 2 | 1 | 1 | 1 | 1 | 1 | 1 | 2 |

Fig. 7B

| AttributionNo | L31 | HdeB | S10 | L22 | S15 | L25 | HNS | L19 | L20 | L29 | S05 | S12 | L13 | L15 |
|---|---|---|---|---|---|---|---|---|---|---|---|---|---|---|
| 1 | 7072.80 | 9086.24 | 11736.57 | 12227.29 | 10139.57 | 10684.43 | 15409.42 | 13003.02 | 13368.76 | 7274.44 | 17473.18 | 12969.20 | 16019.52 | 14981.41 |
| 2 | 7886.11 | 9049.30 | | 12242.26 | 10166.5 | 10676.39 | 15427.41 | 13017.05 | 13284.80 | 7281.45 | 17445.13 | 12983.22 | 16033.55 | 14967.38 |
| 3 | 7854.04 | 9049.20 | | | | 10684.41 | 15437.43 | | 12396.78 | 7288.47 | | | 15966.48 | |
| 4 | | | | | | 10593.37 | 15425.4 | | 13394.81 | 7302.50 | | | 15959.42 | |

Fig. 8A

| Strain\Protein name | L31 | HdeB | S15 | L25 | HNS | L29 | L13 |
|---|---|---|---|---|---|---|---|
| Ec K12 W3110 | 1 | 1 | 1 | 1 | 1 | 1 | 1 |
| Ea_JCM17328T | 2 | 2 | 1 | 4 | 2 | 1-2 | 1 |
| Shigella_dysenteriae_GTC00786T | 1 | 2 | 1 | 1 | 1 | 1-4 | 3 |
| Shigella_flexneri_GTC00780T | 3 | 1 | 1 | 1 | 1 | 1-3 | 1 |
| Shigella_sonnei_GTC00781T | 1 | 1 | 1 | 1 | 1 | 1 | 2 |
| Shigella_boydii_GTC00779T | 1 | 1 | 1 | 3 | 3 | 1 | 3 |
| Ec_O157-1_GTC14546-13 | 1 | 0 | 2 | 2 | 1 | 1 | 1 |
| Ec_O157-2_GTC14550-15 | 1 | 0 | 1 | 1 | 1 | 1 | 1 |
| Ec_O111_GTC14507-2 | 1 | 1 | 1 | 1 | 2 | 1 | 1 |
| Ec_O26_GTC14538-18 | 1 | 1 | 1 | 1 | 2 | 1 | 1 |

Fig. 8B

| Attribution No. | L31 | HdeB | S15 | L25 | HNS | L29 | L13 |
|---|---|---|---|---|---|---|---|
| 1 | 7872.08 | 9066.24 | 10138.566 | 10694.43 | 15409.42 | 7274.44 | 16019.52 |
| 2 | 7886.11 | 9048.20 | 10166.6 | 10676.39 | 15427.412 | 7261.45 | 16033.55 |
| 3 | 7854.04 | ~~9049.30~~ | | 10664.41 | 15437.43 | 7288.47 | 15966.48 |
| 4 | | | | 10593.37 | 15425.4 | 7302.50 | ~~15959.42~~ |

Fig. 10

| name | % | family | genus | species | datacount |
|---|---|---|---|---|---|
| 01_Ea-JCM17382T_0001_3C2[c] | 89.9 | Family I Enterobacteriaceae | Escherichia | coli | 366 |
| B133-Ec-NBRC12713-FA-0001.3B2[c] | 92.5 | Family I Enterobacteriaceae | Escherichia | coli | 194 |
| 01_Sd-GTC00786T_0001_2K2[c] | 99.2 | Family I Enterobacteriaceae | Escherichia | coli | 367 |
| 02_Sf_2a-GTC00780T_0001_2K4[c] | 99.9 | Family I Enterobacteriaceae | Escherichia | coli | 370 |
| 03_Ss-GTC00781T_0001_2L2[c] | 99.9 | Family I Enterobacteriaceae | Escherichia | coli | 354 |
| 05_Sb-GTC00779T_0001_3A1[c] | 90.3 | Family I Enterobacteriaceae | Escherichia | coli | 360 |
| 13_GTC14546-O157-H7--VT2-0001_1K1[c] | 90.9 | Family I Enterobacteriaceae | Escherichia | coli | 350 |
| 15_GTC14550-O157-H7-VT2-0001_1L2[c] | 98.4 | Family I Enterobacteriaceae | Escherichia | coli | 325 |
| 02_GTC14507-O111-H--VT12-0001_1E4[c] | 99.9 | Family I Enterobacteriaceae | Escherichia | coli | 418 |
| 18_GTC14538-O26-H--VT1-0001_2A4[c] | 90.4 | Family I Enterobacteriaceae | Escherichia | coli | 188 |

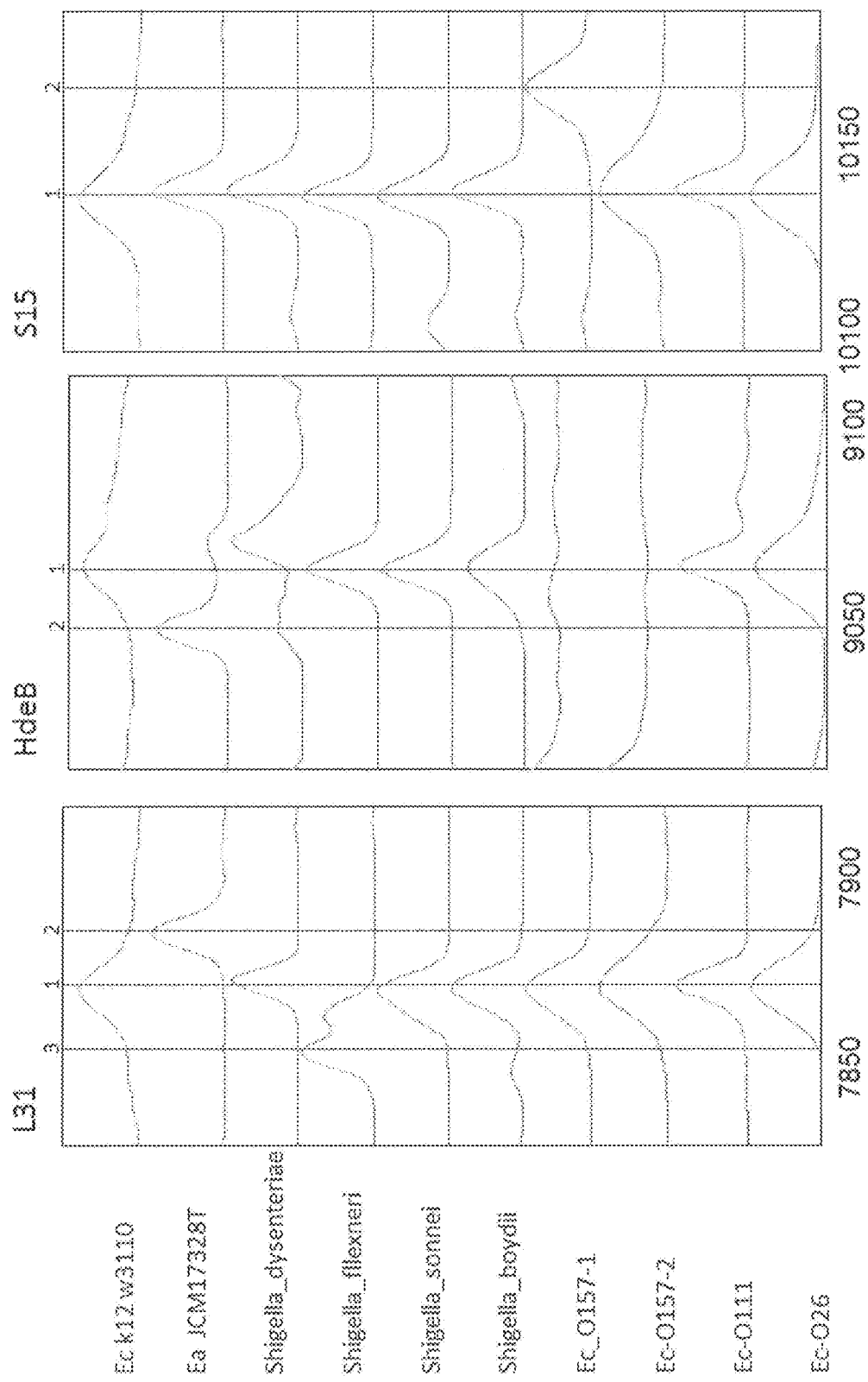

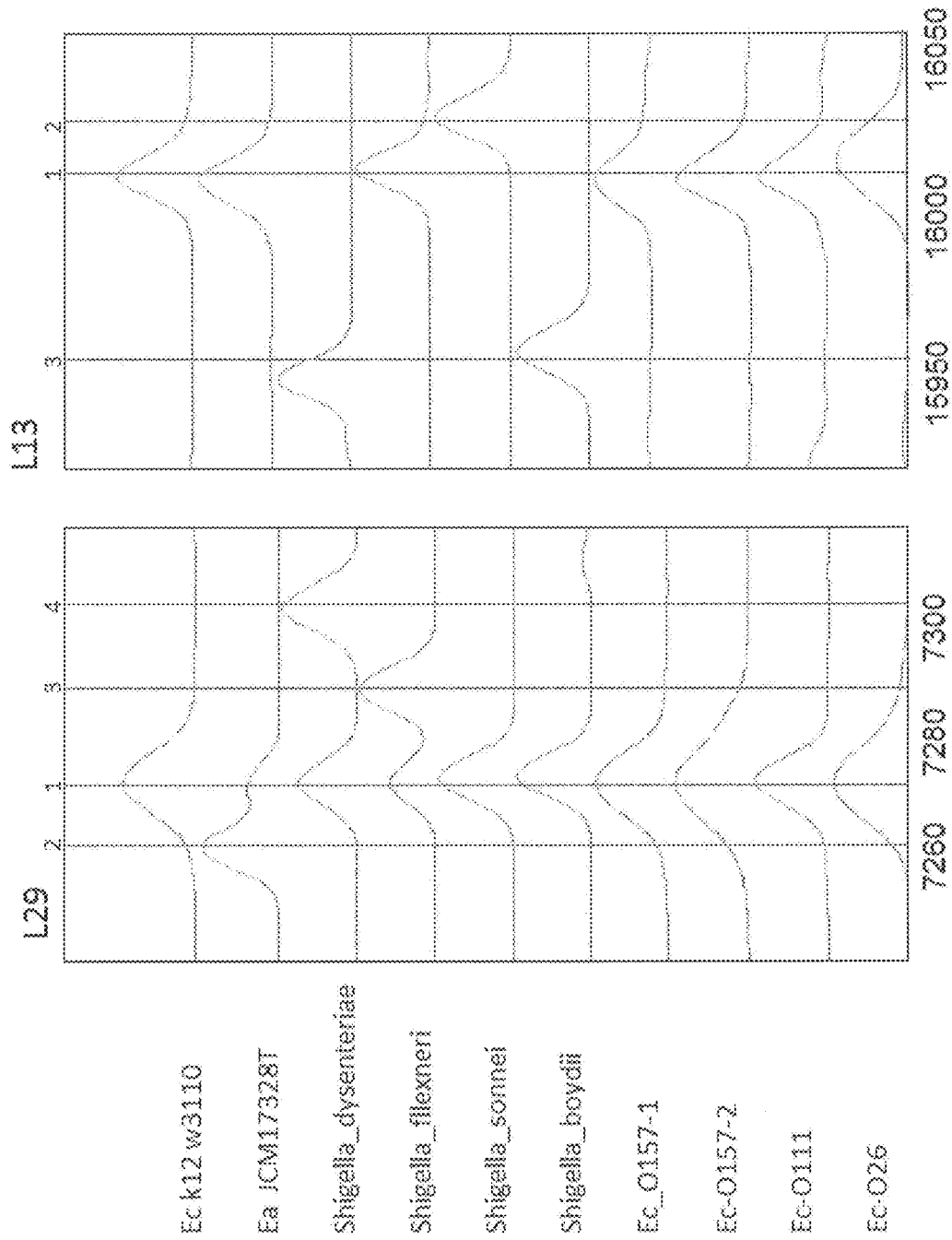

| Strain\Protein name | L29 |
|---|---|
| Ec K12 W3110 | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGCGATGTC GCACGCGTTAAGACTTTACTGAACGAGAAGGCGGGTGCGTAA |
| Ec_JCM17328T | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGTGATGTC GCACGCGTTAAGACTTTACTGACTGAGAAGGCGGGTGCGTAA |
| Shigella_dysenteriae_GTC00786T | ATGAAAGCAAAAGACCTGCGTGAGAAGAGCGTTGAAGAGCTGAACACCGACCTGCTGAACCTGCTGCGTGAGCAG TTCAACCTGCGTATGCAGGCTGCAAGTCGCCAGCTGCAACAGTCTCACCTGTTGAAGCAAGTGCGTCGGCGATGTC GCACGCGTTAAGACTTTACTGAACGAGAACGCGGGTGCGTAA |
| Shigella_flexneri_GTC00780T | ATGAAAGCAAAAGAGCTGCGTGAGAAGAGCATTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGGCATGTC GCACGCGTTAAGACTTTACTGAACGAGAAGGCGGGTGCGTAA |
| Shigella_sonnei_GTC00781T | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGCGATGTC GCACGCGTTAAGACTTTACTGAACGAGAAGGCGGGTGCGTAA |
| Shigella_boydii_GTC00779T | |
| Ec_O157-1_GTC14546-13 | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGCGATGTC GCACGCGTTAAGACTTTACTGAACGAGAAGGCGGGTGCGTAA |
| Ec_O157-2_GTC14550-15 | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGCGATGTC GCACGCGTTAAGACTTTACTGAACGAGAAGGCGGGTGCGTAA |
| Ec_O111_GTC14597-2 | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGGCGATGTC GCACGCGTTAAGACTTTACTGAACGAGAAGGCGGGTGCGTAA |
| Ec_O26_GTC14538-18 | ATGAAAGCAAAAGAGCTGCGTGAGAAGAGCGTTGAAGAGCTGAACACCGAGCTGCTGAACCTGCTGCGTGAGCAG TTCAACCTGCGTATGCAGGCTGCAAGTGGCCAGCTGCAACAGTCTCACCTGTTGAAGCAAGTGCGTCGCGATGTC GCACGCGTTAAGACTTTACTGAACGAGAAGGCGGGTGCGTAA |

Fig. 14C

| Strain \ Protein name | L13 |
|---|---|
| Ec K12 W3110 | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Ea_JCM1732ST | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCCTGCGCGGTAAGCACAAAGCGGAATACACTCGGCACGTAGATACCG<br>GTGATTACATCATCGGTTCTGAACGCTGACAAAGTTGCTGTAACTGGCAACAAGCGTACTGATAAAGTGTACTATCA<br>CCACACCGCACATCGGTGTATCAAACAAGCGGACCTTTGAAGAGATGATTGCTCGCCGTCCTGAGCGTGTGAT<br>TGAAATCGCGGTTAAAGGCATGCTGCCAAAAGGCCCAACTGGGTCGTGCTATGTTCCGTAAACTGAAAGTTTACGC<br>GGGTAACGAGCATAACCACGCGGCACAGCAACCGCAAGTTCTTGACATCTAA |
| Shigella_dysenteriae_GTC00788 | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Shigella_flexneri_GTC00780T | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Shigella_sonnei_GTC00781T | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Shigella_boydii_GTC00779T | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Ec_O157-1_GTC14546-13 | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Ec_O157-2_GTC14550-15 | ATGAAAACTTTTACAGCTAAACCAGAAACCGTAAAACGCGACTGGTATGTTGTTGACGCGACCGGTAAAACTCTGG<br>GCCGTCTGGCTACTGAACTGGCTCGTCGCTGCGCGGTAAGCACAAAGCGGAATACACTCGGCACGTAGATACCG<br>GTGATTACATCATCGGTTCTGAACGCTGACAAAGTTGCTGTAACCGGCAACAAGCGTACTGACAAAGTGTACTATCA<br>CCACACCGGCCACATCGGTGGTATCAAACAAGCGGACCTTTGAAGAGATGATTGCTCGCCGTCCTGAGCGTGTGAT<br>TGAAATCGCGGTTAAAGGCATGTTGCCAAAAGGCCCGCTGGGTCGTGCTATGTTCCGTAAACTGAAAGTTTACGC<br>GGGTAACGAGCACAACCACGCGGCACAGCAACCGCAAGTTCTTGACATCTAA |
| Ec_O111_GTC14507-2 | |
| Ec_O26_GTC14538-18 | |

Fig. 14D

| Strain \ Protein name | S15 |
|---|---|
| Ec K12 W3110 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Ea JCM17328T | ATGTCTCTAAGTACTGAAGCAACAGCTAAAATCGTTTCTGAGTTTGGTCGTGACGCAAACGACACTGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Shigella_dysenteriae_GTC00788 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTATACCCAGCTCATCGAGCGCCTGGGTCTGCGTCGGTAA |
| Shigella_flexneri_GTC00780T | ATGTCTCTAAGTACTGAAGCAACAGCTAAAATCGTTTCTGAGTTTGGTCGTGACGCAAACGACACCGGTTCTACTG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Shigella_sonnei_GTC00781T | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Shigella_boydii_GTC00779T | |
| Ec_O157-1_GTC14546-13 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCGGCTCATCGAGCGCCTGGGTCTGCGTCGGTAA |
| Ec_O157-2_GTC14550-15 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Ec_O111_GTC14507-2 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |
| Ec_O26_GTC14538-18 | ATGTCTCTAAGTACTGAAGCAACAGCTAAAATCGTTTCTGAGTTTGGTCGTGACGCAAACGACACCGGTTCTACCG<br>AAGTTCAGGTAGCACTGCTGACTGCACAGATCAACCACCTGCAGGGCCACTTTGCAGAGCACAAAAAAGATCACC<br>ACAGCCGTCGTGGTCTGCTGCGGCATGGTTTCTCAGCGTCGTAAACTGCTCGACTACCTGAAACGTAAAGACGTAG<br>CACGTTACACCCAGCTCATCGAGCGCCTGGGTCTGCGTCGGTAA |

Fig. 14E

| Strain\Protein name | L25 |
|---|---|
| Ec_K12_W3110 | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCGCCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Ec_JCM17328T | ATGTTTACTATCAACGCAGAAGTACGTAAAGAGCAGGGTAAGGGTGCGAGCCGCCGCCTGCGTACCGCTAACAAA<br>TTCCCGGCAATCATCTACGGTGGCAACGAAGCTCGGCTGGCTGTTGCTCTGGGTCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ATGTACAGCGTCACCCGTACAAACGAAGCTGCTGCAGATCGACTTCGTTCGCGCTTAA |
| Shigella_dysenteriae_GTC00788 | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAG |
| Shigella_flexneri_GTC00780T | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATG<br>CAAGCTAAAGCTGAATTCTACAGCGAAGTTCTAACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Shigella_sonnei_GTC00781T | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCGCCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Shigella_boydii_GTC00779T | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Ec_O157-1_GTC14546-13 | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATT<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Ec_O157-2_GTC14550-15 | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |
| Ec_O111_GTC14567-2 | ATGTTTACTATCAACGCAGAAGTACGTAAAGAGCAGGGTAAGGGTGCGAGCCGCCGCCTGGTATCGAGCTGATCACGACAAAGTCATGAACATG<br>TTCCCGGCAATCATCTACGGTGGCAAAGAAGCACCGCTGGCTATCGAGCTGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCCCGTACAAACGAAGCTGCAGCACATCGACTTCGTTCGCGCTTAA |
| Ec_O26_GTC14538-18 | ATGTTTACTATCAACGCAGAAGTACGTAAAGAGCAGGGTAAGGGTGCGAGCCGCCGCCTGCGTGCCGCTAACAAG<br>TTCCCGGCAATCATCTACGGTGGCAAAGAAGCACCGCTGGCTATCGAGCTGGATCACGACAAAGTCATGAACATG<br>CAAGCTAAAGCTGAATTCTACAGCGAAGTTCTGACCATCGTTGTTGACGGTAAAGAAATCAAAGTTAAAGCTCAGG<br>ACGTACAGCGTCACCCGTACAAACGAAGCTGCAGCACATCGACTTCGTTCGCGCTTAA |

Fig. 14F

| Strain\Protein name | HNS |
|---|---|
| Ec_K12_W3110 | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAACGTCGCGAAGAAGAAAGCGCGGCTGCTGCTGAAGT TGAAGAGCGCACTCGTAAACTGCAGCAATATCGCGAAATGCTGATCGCTGACGGTATTGACCCGAACGAACTGCT GAATAGCCTTGCTGCCGTTAAATCTGGCACCAAAGCTAAACGTGCTCAGCGTCCGGCAAAATATAGCTACGTTGA CGAAAACGGCGAAACTAAAACGTGGACTGGCCAAGGCCGTACTCCAGCTGTAATCAAAAAAGCAATGGATGAGCAA GGTAAATCGCTCGACGATTTCCTGATCAAGCAATAA |
| Ea_JCM17328T | ATGAGCGAAGCACTTAAAATTCTGAACAACATCCGTACTCTTCGTGCACAGGCAAGAGAATGTACGCTTGAAACGC TGGAAGAAATGCTGGAAAAATTAGAAGTCGTTGTTAACGACGGTCGCGAAGAAGAAAGCGCGGCGGGTGCTGAAG TTGAAGAACGTACTCGTAAACTGCAGCAATATCGTGAAATGCTGATCGCTGACGGTATTGACCCGAACGAACTGCT GAATAGCATGGCTGCTGTTAAATCTGGCACTAAAGCTAAACGTGCACAACGTCCGGCGAAATATAGCTACGTTGAC GAAAACGGCGAAACTAAAACCTGGACTGGCCAAGGCCGTACTCCGGCAGTAATCAAAAAAGCAATGGACGAGCAA GGTAAATCTCTCGACGATTTCCTGATCCAGCAATAA |
| Shigella_dysenteriae_GTC00788 | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAACGTCGCGAAGAAGAAAGCGCGGCTGCTGCTGAAGT TGAAGAGCGTACTCGTGAAACTGCAGCAATATCGCGAAATGCTGATCGCTGACGGTATTGACCCGAACGAACTGCT GAATAGCCTTGCTGCCGTTAAATCTGGCACCAAAGCTAAACGTGCTCAAGGTCCGGCAAAATATAGCTACGTTGAC GAAAACGGCGAAACTAAAACCTGGACTGGCCAGGGCCGTACTCCAGCTGTAATCAAAAAAGCAATGGATGAGCAA GGTAAATCGCTCGACGATTTCCTGATCAAGCAATAA |
| Shigella_flexneri_GTC00780T | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAAGGTCGCGAAGAAGAAAGCGCGGCTGCTGCTGAAGT TGAAGAGCGCACTCGTAAGCTGCAGCAATATCGCGAAATGCTGATCGCTGACGGTATTGACCCGAACGAACTGCT GAATAGCCTTGCTGCCGTTAAATCTGGCACCAAAGCTAAACGTGCTCAGCGTCCGGCAAAATATAGCTACGTTGA CGAAAACGGCGAAACTAAAACCTGACTGGCCAAGGCCGTACTCCAGCTGTAATCAAAAAAGCAATGGATGAGCAA GGTAAATCGCTCGACGATTTCCTGATCAAGCAATAA |
| Shigella_sonnei_GTC00781T | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAACGTCGCGAAGAAGAAAGCGCGGCTGCTGCTGAAGT TGAAGAGCGCACTCGTAAGCTGCAGCAATATCGCGAAATGCTGATCGCTGACGGTATTGACCCGAACGAACTGCT GAATAGCCTTGCTGCCGTTAAATCTGGCACCAAAGCTAAACGTGCTCAGCGTCCGGCAAAATATAGCTACGTTGA CGAAAACGGCGAAACTAAAACCTGGACTGGCCAAGGCCGTACTCCAGCTGTAATCAAAAAAGCAATGGATGAGCAA GGTAAATCGCTCGACGATTTCCTGATCAAGCAATAA |
| Shigella_boydii_GTC00779T | |
| Ec_O157-1_GTC14546-13 | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAACGTCGCGAAGAAGAAAGCGCGGCTGCTGCTGAAGT TGAAGAGCGCACTCGTAAACTGCAGCAATATCGCGAAATGCTGATCGCTGACGGTATTGACCCGAACGAGCTGCT GAATAGCCTTGCTGCCGTTAAATCTGGCACCAAAGCTAAACGTGCTCAGCGTCCGGCAAAATATAGCTACGTTGA CGAAAACGGCGAAACTAAAACCTGGACTGGCCAGGGCCGTACTCCAGCTGTAATCAAAAAAGCAATGGATGAGCA AGGTAAATCGCTCGACGATTCCTGATCAAGCAATAA |
| Ec_O157-2_GTC14550-15 | ATGAGCGAAGCACTTAAAATTCTGAACAACATCCGTACTCTTCGTGCGCAGGCAAGAGAATGTACACTTGAAACGC TGGAAGAAATGCTGGAAAAATTAGAAGTTGTTGTTAACGAACGTCGCGAAGAAGAAAGCGCGGCTGCTGCTGAAGT TGAAGAGCGCACTCGTAAACTGCAGCAATATCGCGAAATGCTGATCGCTGACGGTATTGACCCGAACGAGCTGCT GAATAGCCTTGCTGCCGTTAAATCTGGCACCAAAGCTAAACGTGCTCAGCGTCCGGCAAAATATAGCTACGTTGA CGAAAACGGCGAAACTAAAACCTGGACTGGCCAGGGCCGTACTCCAGCTGTAATCAAAAAAGCAATGGATGAGCA AGGTAAATCGCTCGACGATTCCTGATCAAGCAATAA |
| Ec_O111_GTC14587-2 | |
| Ec_O26_GTC14538-18 | |

Fig. 15A

| Strain \ Protein name | L31 | HdeB | S15 |
|---|---|---|---|
| Ec_K12_W3110 | MKKDHPKYEEITASCSCGNVMKIRST VGHDLNLDVCSKCHPFFTGKGRDVA TGGRVDRFNKRFNIPGSK | MNISSLRKAFIFMGAVAALSLVNAQSA LAANESAKDMTCQEFIDLNPKAMTPV AWWMLHEETVYKGGDTVTLNETDLT QIPKVIEYCKKNPQKNLYTFKNGASN DLPN | MSLSTEATAKIVSEFGRDANDTGSTEV QVALLTAQINHLQGHFAEHKKDHHSR RGLLRMVSQRRKLLDYLKRKDVARYT QLIERLGLRR |
| Ea_JCM17328T | MKKDHPKYEEITATCSCGNVMKIRST VGHDLNLDVCSKCHPFFTQLQRDVA TGGRVDRFNKRFNIPGSK | MNISSLRKAIVFIGAVAALSLANAGSVL AANESAKDMTCQEFIDLNPKAMTPVA WWMLHEETVYKGGDTVTLNETDLTQI PKVIEYCKKNPQKNLYSFKDNLANVL PN | MSLSTEATAKIVSEFGRDANDTGSTEV QVALLTAQINHLQGHFAEHKKDHHSR RGLLRMVSQRRKLLDYLKRKDVARYT QLIERLGLRR |
| Shigella_dysenteriae_GTC00788T | MKKDHPKYEEITASCSCGNVMKIRST VGHDLNLDVCSKCHPFFTGKQRDVA TGGRVDRFNKRFNIPGSK | MNISSLRKAFIFMGAVAALSLVNAQSA LAANESAKDMTCQEFIDLNPKAMTPV AWWMLHEETVYKGGDTVTLNETDLT QIPKVIEYCKKNPQKNLYTFKNGASNDL PN | MKKDHPKYEEITASCSCGNVMKIRST VGHDLNLDVCSKCHPFFTGKQRDVA TGGRVDRFNKRFNIPGSK |
| Shigella_flexneri_GTC00780T | MKKDHPKYEEITASCSCGNVMKIRSTV GHDLNLDVCSKCHPFFTGKQRDVAT GGRVDRFNKRFNIPGSK | MNISSLRKAFIFMGAVAALSLVNAQSA LAANESAKDMTCQEFIDLNPKAMTPV AWWMLHEETVYKGGDTVTLNETDLT QIPKVIEYCKKNPQKNLYTFKNGASN DLPN | MSLSTEATAKIVSEFGRDANDTGSTEV QVALLTAQINHLQGHFAEHKKDHHSR RGLLRMVSQRRKLLDYLKRKDVARYT QLIERLGLRR |
| Shigella_sonnei_GTC00781T | MKKDHPKYEEITASCSCGNVMKIRST VGHDLNLDVCSKCHPFFTGKQRDVA TGGRVDRFNKRFNIPGSK | MNISSLRKAFIFMGAVAALSLVNAQSA LAANESAKDMTCQEFIDLNPKAMTPV AWWMLHEETVYKGGDTVTLNETDLT QIPKVIEYCKKNPQKNLYTFKNGASN DLPN | MSLSTEATAKIVSEFGRDANDTGSTEV QVALLTAQINHLQGHFAEHKKDHHSR RGLLRMVSQRRKLLDYLKRKDVARYT QLIERLGLRR |
| Shigella_boydii_GTC00779T | | MNISSLRKAFIFMGAVAALSLVNAQSA LAANESAKDMTCQEFIDLNPKAMTPV AWWMLHEETVYKGGDTVTLNETDLT QIPKVIEYCKKNPQKNLYTFKNGASN DLPN | |
| Ec_O157-1_GTC14546-13 | MKKDHPKYEEITASCSCGNVMKIRST VGHDLNLDVCSKCHPFFTGKQRDVA TGGRVDRFNKRFNIPGSK | MGYKINESLRKAFIFMGAVAALSLVNA QSALAANESAKDMTCQEFIDLNPKAM TPVAWWMLHEETVYKGGDTVTLNET DLTQIPKVIEYCKKNPQKNLYTFKNQA SNDLPN | MSLSTEATAKIVSEFGRDANDTGSTEV QVALLTAQINHLQGHFAEHKKDHHSR RGLLRMVSQRRKLLDYLKRKDVARYT QLIERLGLRR |
| Ec_O157-2_GTC14550-15 | MKKDHPKYEEITASCSCGNVMKIRST VGHDLNLDVCSKCHPFFTGKQRDVA TGGRVDRFNKRFNIPGSK | MGYKINESLRKAFIFMGAVAALSLVNA QSALAANESAKDMTCQEFIDLNPKAM TPVAWWMLHEETVYKGGDTVTLNET DLTQIPKVIEYCKKNPQKNLYTFKNQA SNDLPN | MSLSTEATAKIVSEFGRDANDTGSTEV QVALLTAQINHLQGHFAEHKKDHHSR RGLLRMVSQRRKLLDYLKRKDVARYT QLIERLGLRR |
| Ec_O111_GTC14507-2 | | | MSLSTEATAKIVSEFGRDANDTGSTEV QVALLTAQINHLQGHFAEHKKDHHSR RGLLRMVSQRRKLLDYLKRKDVARYT QLIERLGLRR |
| Ec_O26_GTC14538-18 | | | MSLSTEATAKIVSEFGRDANDTGSTEV QVALLTAQINHLQGHFAEHKKDHHSR RGLLRMVSQRRKLLDYLKRKDVARYT QLIERLGLRR |

Fig. 15B

| Strain\Protein name | L25 | HNS | L28 |
|---|---|---|---|
| Ec_K12_W3110 | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSVEELNTELLNLLREQFNLRMQAASGQLQQSHLLKQVRRDVARVKTLLNEKAGA |
| Ea_JCM17328T | MFTINAEVRKEQGKGASRRLRTANKFPAIIYGGNEAPLAVALGHDKVMNMQVKAEFYSEVLTIVVDGKEIKVKAQDVQRHPYKPKLLHIDFVRA | MSEALKILNNIRTLRAQARECTLETLEEMLEKLEVVVNERREEESAAAAEVEERTRKLQQYREMLADGIDPNELLNSMAAVKSGTKAKRAQRPAKYSYVDENGETKTWTGQGRTPAVIKKAMDEQGKSLDDFLIQG | MKAKELREKSVEELNTELLNLLREQFNLRMQAASGQLQQSHLLKQVRRDVARVKTLLTEKAGA |
| Shigella_dysenteriae_GTC00786T | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSVEELNTELLNLLREQFNLRMQVASGQLQQSHLLKQVRRDVARVKTLLNEKAGA |
| Shigella_flexneri_GTC00780T | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSIEELNTELLNLLREQFNLPMQAASGQLQQSHLLKQVRRDVARVKTLLNEKAGA |
| Shigella_sonnei_GTC00781T | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSVEELNTELLNLLREQFNLRMQAASGQLQQSHLLKQVRRDVARVKTLLNEKAGA |
| Shigella_boydii_GTC00779T | MFTINAEVRKEQGKGASRRLRAANKFPAIIYGGKEAPLAIELDHDKVMNMQAKAEFYSEVLAIVVDGKEIKVKAQDVQRHPYKPKLQHIDFVRA | | |
| Ec_O157-1_GTC14546-13 | MFTINAEVRKEQGKGASRRLRAANKFPAIIYGGKEAPLAIELDHDKVMNIQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSVEELNTELLNLLREQFNLRMQAASGQLQQSHLLKQVRRDVARVKTLLNEKAGA |
| Ec_O157-2_GTC14550-15 | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | MSEALKILNNIRTLRAQARECTLETLEEMLEKLEVVVNERREEESAAAAEVEERTRKLQQYREMLIADGIDPNELLNSLAAVKSGTKAKRAQRPAKYSYVDENGETKTWTGQGRTPAVIKKAMDEQGKSLDDFLIKQ | MKAKELREKSVEELNTELLNLLREQFNLRMQAASGQLQQSHLLKQVRRDVARVKTLLNEKAGA |
| Ec_O111_GTC14557-2 | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | | MKAKELREKSVEELNTELLNLLREQFNLRMQAASGQLQQSHLLKQVRRDVARVKTLLNEKAGA |
| Ec_O26_GTC14536-18 | MFTINAEVRKEQGKGASRRLRAANKFPAIIYGGKEAPLAIELDHDKVMNMQAKAEFYSEVLTIVVDGKEIKVKAQDVQRHPYKPKLQHIDFVRA | | MKAKELREKSVEELNTELLNLLREQFNLRMQAASGQLQQSHLLKQVRRDVARVKTLLNEKAGA |

Fig. 15C

| Strain\Protein name | L13 |
|---|---|
| Ec_K12_W3110 | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMFRKLKVYAGNEHNHAAQQPQVLDI |
| Es_JCM17328T | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMFRKLKVYAGNEHNHAAQQPQVLDI |
| Shigella_dysenteriae_GTC00736T | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMSRKLKVYAGNEHNHAAQQPQVLDI |
| Shigella_flexneri_GTC00780T | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMFRKLKVYAGNEHNHAAQQPQVLDI |
| Shigella_sonnei_GTC00781T | MKTFTAKPETVKRDWYVVDATGKTLGRLATELARRLRGKHKAEYTPHVDTGDYIIVLNADKVAVTGNKRTDKVYYHHTGHIGGIKQVSFEEMARRPERVIEIAVKGMLPKGPLGRAMFRKLKVYAGNEHNHAAQQPQVLDI |
| Shigella_boydii_GTC00779T | MKTFTAKPETVKRDWYVVDATGKTLGRLATELARRLRGKHKAEYTPHVDTGDYIIVLNADKVAVTGNKCTDKVYYHHTGHIGGIKQATFEEMARRPERVIEIAVKGMLPKGPLGRAMFRKLKVYAGNEHNHAAQQPQVLDI |
| Ec_O157-1_GTC14546-13 | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMFRKLKVYAGNEHNHAAQQPQVLDI |
| Ec_O157-2_GTC14550-15 | MKTFTAKPETVKRDWYVVDATGKTLGRLATELARRLRGKHKAEYTPHVDTGDYIIVLNADKVAVTGNKRTDKVYYHHTGHIGGIKQATFEEMARRPERVIEIAVKGMLPKGPLGRAMFRKLKVYAGNEHNHAAQQPQVLDI |
| Ec_O111_GTC14507-2 | |
| Ec_O26_GTC14538-18 | |

METHOD FOR DISCRIMINATING MICROORGANISM

CROSS REFERENCE TO RELATED APPLICATIONS

This application is a National Stage of International Application No. PCT/JP2016/060867, filed on Mar. 31, 2016.

TECHNICAL FIELD

The present invention relates to a method for discriminating a microorganism using mass spectrometry.

BACKGROUND ART

*Shigella* is the causative bacterium for shigellosis and first isolated by Kiyoshi Shiga in 1898. At that time, an epidemic of dysentery occurred every year, the same bacterium was isolated from 34 of 36 patients with dysentery, and the bacterium was *Shigella dysenteriae*, which was discovered later. Subsequently, *Shigella flemeri, Shigella boydii,* and *Shigella sonnei* were discovered, and at present, 4 species of the genus *Shigella* exist.

However, the homology between DNAs of *Shigella* bacteria and *Escherichia coli* is 85% or more on average (Non Patent Literature 1), and this value is generally shown in strains in the same species. Classification of *Shigella* bacteria is based on medical importance rather than taxonomy, and *Shigella* bacteria is the same genospecies as for *Escherichia coli* based on bacterial taxonomy, so that 4 bacterial species among the genus *Shigella* are actually only a biotype. Therefore, discrimination between *Shigella* bacteria and *Escherichia coli* is very hard, but the genus *Shigella* is independent of the genus *Escherichia* based on medical importance and habit (Non Patent Literature 2).

*Shigella* have pathogenicity to humans and cause bacterial diarrhea although the severity varies depending on bacterial species. It has been known that infection is established by a very small amount of bacteria (Non Patent Literature 3). For these reasons, *Shigella* bacteria must be managed in the food field and the medical field as food poisoning bacteria, and development of rapid detection and an identification and discrimination technology has been required.

*Escherichia albertii* (hereinafter also referred to as "*E. alhertii*") is a species that was formally published as a novel species in 2003 (Non Patent Literature 4). This species shows characteristics that are likely to be misidentified as *Escherichia coli*, such as no characteristic biochemical properties and having the intimin gene eaeA (Non Patent Literature 5). If it is focused on having genes of eae and toxin 2f, there is the possibility that the strain may be misidentified as enterohe orrhagic *Escherichia coli* (Non Patent Literatures 6 and 7).

For these reasons, *Escherichia albertii* must also be managed in the food field and the medical field as food poisoning bacteria, and development of rapid detection and an identification and discrimination technology has been required.

Heretofore, as a method for discriminating *Escherichia coli*. the genus *Shigella*, and *E. albertii* PCR (Non Patent Literatures 6, 8, and 9), pan-genome analysis (Non Patent Literatures 10 and 11), multi-locus sequence typing method (Non Patent Literatures 6 and 12) and the like have been reported. However, these methods pose a problem that complicated operations are needed and a time is required.

Meanwhile, in the recent years, a microorganism identification technology using matrix-assisted laser desorption/ionization time-of-flight mass spectrometry (MALDI-TOFMS) has been rapidly spreading in the clinical field and the food field. This method is a method of identifying a microorganism based on a mass spectrum pattern obtained using a trace amount of a microorganism sample, and an analysis result can be obtained in a short time. In addition, continuous analysis of multiple specimens is easily carried out, so that simple and quick microorganism identification is possible.

CITATION LIST

Patent Literature

Patent Literature 1: JP 2006-191922 A
Patent Literature 2: JP 2013-085517 A
Patent Literature 3: JP 2015-184020 A

Non Patent Literature

Non Patent Literature 1: BRENNER, D. J., Fanning, G. R., Miklos, G. V., & Steigerwalt, A. G., International Journal of Systematic and Evolutionary Microbiology, (1973), 23(1), 1-7.
Non Patent Literature 2: Manual for Test and Diagnosis of *Shigella*—National Institute of infectious Diseases. [searched on Mar. 18, 2016], Internet <URI:www.nih.go.jp/niid/images/lab-manual/*shigella*.pdf>
Non Patent Literature 3: Comprehensive Survey of Ensuing Food Safety 2010 "Report on Literature Review on Infections Mediated by Food (excerpt)", prepared by TORAY Research Center, Inc., [searched on Mar. 18, 2016], Internet <https://www.fsc.go.jp/sonota/azard/H22_10.pdf>
Non Patent Literature 4: Huys. G. et al., International journal of systematic and evolutionary microbiology, 2003, 53(3), 807-810.
Non Patent Literature 5: Ooka, I. et al., Emerg Infect Dis. 2012, 18(3), 488-492.
Non Patent Literature 6: Hyma, K. E. et al., Journal of bacteriology, 2005, 187(2), 619-628.
Non Patent Literature 7: Murakami, K. et al., Japanese journal of infectious diseases, 2014, 67(3), 204-208.
Non Patent Literature 8: Watanabe, H. A. R. U. O et al., 1990. Journal of bacteriology, 172(2), 619-629.
Non Patent Literature 9: Thiem, V. D. et al., Journal of clinical microbiology, 2004, 42(5), 2031-2035.
Non Patent Literature 10: Lukjancenko, O. et al., Microbial ecology, 2010, 60(4), 708-720.
Non Patent Literature 11: Rasko, D. A. et al., Journal of bacteriology, 2008, 190(20), 6881-6893.
Non Patent Literature 12: Oaks, J. L. et al., Escherichia alhertii in wild and domestic birds, 2010.
Non Patent Literature 13: Dallagassa, C. B. et al, Genet Mol Res, 2014, 13(1), 716-22.
Non Patent Literature 14: Deng, J. et al., Journal of thoracic disease, 2014, 6(5), 539.
Non Patent Literature 15: Khot, P. D., & Fisher, M. A., Journal of clinical microbiology, 2013, 51(11), 3711-3716.

SUMMARY OF INVENTION

Technical Problem

Heretofore, it has been attempted to discriminate *Listeria* bacteria using MALDI-TOF MS by a plurality of research groups (Non Patent Literatures 13, 14, and 15). In Non Patent Literatures 13 and 14, some of strains of *Escherichia coli* and *Shigella* bacteria could not be discriminated, and in Non Patent Literature 15, 90% of samples could be correctly discriminated, but 10% showed misdiscrimination between *Escherichia coli* and *Shigella sonnei*. Regarding the peaks used in these reports, from which proteinach peak or each biomarker peak originates is not determined, lacking in the theoretical basis of identification and discrimination as well as reliability, and unified views have not yet been obtained (the results are different from research group to research group). In other words, a highly reliable marker protein that can be suitably used for discrimination of *Escherichia coli, Shigella* bacteria, and *E. albertii* has not yet been established.

Patent Literature 1 shows that utilizing the fact that about half of peaks obtained by mass spectrometry of microbial cells are derived from ribosomal proteins, a method of attributing the type of protein from which a peak is derived by associating a mass-to-charge ratio of the peak obtained by mass spectrometry with a calculated mass estimated from the amino acid sequence obtained by translating base sequence information of ribosomal protein genes (S10-GERMS method) is useful. According to this method, it is possible to perform microorganism identification with high reliability based on the theoretical basis by using mass spectrometry and attached software (Patent Literature 2).

We have found biomarkers that quickly discriminate *Escherichia coli* O157, O26, and O111 (Patent Literature 3), but these hiomarkers are insufficient for discrimination between *Escherichia coli, Shigella* bacteria, and *E. albertii*.

A technical problem to be solved by the present invention is to provide a highly reliable biomarker based on genetic information that is useful for discrimination of *Escherichia coli, Shigella* bacteria, and *E. albertii*.

Solution to Problem

As a result of diligent discussion, the present inventors have found that 13 ribosomal proteins S5, L15, S13, L31, L22, L19, L20, L13, S15, L25, HNS, HdeB, and L29 are useful as a marker protein for discriminating which bacterial species of *Escherichia coli, Shigella* bacteria, and *Escherichia albertii* is contained in a sample by mass spectrometry, that *Escherichia coli, Shigella* bacteria, and *Escherichia albertii* can be discriminated by using at least one of these ribosomal proteins, and that *Escherichia coli, Shigella* bacteria, and *Escherichia albertii* can be discriminated reproducibly and quickly in particular by using at least one of 7 ribosomal proteins L31, L13, S15, L25, HNS, HdeB, and L29 among these 13 ribosomal proteins.

That is, a method for discriminating a microorganism according to the present invention, which has been made to solve the above problem, includes:

a) a step of subjecting a sample containing a microorganism to mass spectrometry to obtain a mass spectrum;

b) a reading step of reading a mass-to-charge ratio m/z of a peak derived from a marker protein from the mass spectrum: and c) a discrimination step of discriminating which bacterial species of *Escherichia coli, Shigella* bacteria, and *Escherichia albertii* the microorganism contained in the sample contains based on the mass-to-charge ratio m/z, whererin at least one of 13 ribosomal proteins S5, L15, S13, L31, L22, L19, L20, L13, S15, L25, HNS, HdeB, and L29 is used as the marker protein.

Particularly in the method for discriminating a microorganism, it is preferable to use at least one of 7 ribosomal proteins L31, L13, S15, L25, HNS, HdeB, and L29 among the 13 ribosomal proteins as the marker protein, and it is particularly preferable to use 2 ribosomal proteins L13 and L29.

The method for discriminating a microorganism is suitable as a method for discriminating one of *Escherichia albertii, Shigella* dysenteriae, *Shigella flexneri, Shigella sonnei, Shigella boydii*, and *Escherichia coli* as the bacterial species.

Specifically, when the bacterial species to be discriminated in the discrimination step is *Shigella* bacteria, at least one of a group consisting of ribosomal proteins L29 and L13 and a group consisting of ribosomal proteins L31, HdeB, and L13 is contained as the marker protein.

When the bacterial species to be discriminated in the discrimination step is *Escherichia albertii*, at least one of a group consisting of ribosomal proteins L31, HdeB, L25, and HNS, a group consisting of ribosomal proteins L25 and S15, and a ribosomal protein L29 is contained as the marker protein.

Furthermore, when the bacterial species to be discriminated in the discrimination step is *Shigella dysenteriae*, at least one of ribosomal protein HdeB, L29, and L13 is contained as the marker protein.

When the bacterial species to be discriminated in the discrimination step is *Shigella flexneri*, at least one of ribosomal proteins L31 and L29 is contained as the marker protein.

When the bacterial species to be discriminated in the discrimination step is *Shigella sonnei*, at least a ribosomal protein L13 is contained as the marker protein.

When the bacterial species to be discriminated in the discrimination step is *Shigella boydii*, at least one of ribosomal proteins L25, HNS, and L13 is used as the marker protein.

In the above method for discriminating a microorganism, if a cluster analysis is used in which a mass-to-charge ratio m/z of peaks derived from at least ribosomal proteins HdeB, HNS, and L29 is used as an index, it is possible to accurately discriminate which of *E. albertii, Shigella dysenteriae, Shigella flexneri, Shigella sonnei, Shigella boydii*, and *Escherichia coli* the microorganism contained in the sample is.

Furthermore, if a cluster analysis is used in which a mass-to-charge ratio m/z of peaks derived from at least ribosomal proteins L31, L13, S15, L25, HNS, HdeB, and L29 is used as an index, it is possible to more accurately discriminate which of *Escherichia albertii, Shigella dysenteriae, Shigella flexneri, Shigella sonnei, Shigella boydii*, and *Escherichia coli* the microorganism contained in the sample is.

In this case, it is preferable to further include a step of creating a dendrogram representing a discrimination result by the cluster analysis.

Advantageous Effects of Invention

In the method for discriminating a microorganism according to the present invention described above, a ribosomal protein having a mutation peculiar to *Escherichia coli, Shigella bacteria*, and *E. albertii* is used as a marker protein, and therefore, which bacterial species of *Escherichia coli, Shigella* bacteria, and *Escherichia albertii* the microorganism contained in the sample contains can be reproducibly and quickly discriminated.

By using a ribosomal protein having a mutation peculiar to *Escherichia coli, Shigella bacteria*, and *Escherichia albertii* as a marker protein and carrying out cluster analysis using a mass-to-charge ratio m/z of a peak derived from the marker protein on the mass spectra as an index, which bacterial species of *Escherichia coli, Shigella* bacteria, and *Escherichia albertii* the microorganism contained in a plurality of samples is can be collectively discriminated.

BRIEF DESCRIPTION OF DRAWINGS

FIG. 1 is a block diagram showing principal units of a microorganism discrimination system used in a method for discriminating a microorganism according to the present invention.

FIG. 2 is a flowchart showing an example of a procedure for the method for discriminating a microorganism according to the present invention.

FIG. 3 is a diagram showing a list of bacterial species names and strain names of *Escherichia coli, Shigella bacteria*, and *E. albertii* used in Example.

FIG. 4 is a diagram showing a list of primers used in Example.

FIG. 5 is a diagram showing the mass of each amino acid.

FIG. 6A is a diagram showing a list of theoretical mass values and actual measurement values by MALDI-TOF-MS of 14 ribosomal proteins in *Escherichia coli, Shigella* bacteria, and *Escherichia albertii* used in Example.

FIG. 6B is a diagram showing the relationship between the attribution number in FIG. 6A and the theoretical mass value of each ribosomal protein, FIG. 7A is a diagram showing a list of attribution of actual measurement values of 14 ribosomal proteins in *Escherichia coli, Shigella* bacteria, and *Escherichia albertii* used in Example.

FIG. 7B is a diagram showing the relationship between the attribution number in FIG. 7A and the theoretical mass value of each ribosomal protein.

FIG. 8A is a diagram showing a list of attribution of actual measurement values of 7 ribosomal proteins in *Escherichia coli, Shigella* bacteria, and *Escherichia albertii* used in Example.

FIG. 8B is a diagram showing the relationship between the attribution number in FIG. 8A and the theoretical mass value of each ibosomal protein.

FIG. 10 is a discrimination result by a fingerprint method (SARAMIS).

FIG. 11A is a peak chart obtained by MALDI-TOF MS measurement (part 1).

FIG. 11C is a peak chart obtained by MALDI-TOF MS measurement (part 3),

FIG. 14A is a DNA sequence listing (part 1).
FIG. 14B is a DNA sequence listing (part 2),
FIG. 14C is a DNA sequence listing (part 3).
FIG. 14D is a DNA sequence listing (part 4).
FIG. 14E is a DNA sequence listing (part 5).
FIG. 14F is a DNA sequence listing (part 6).
FIG. 15A shows amino acid sequences (part 1).
FIG. 15B shows amino acid sequences (part 2)
FIG. 15C shows amino acid sequences (part 3).

DESCRIPTION OF EMBODIMENTS

Figure 9:
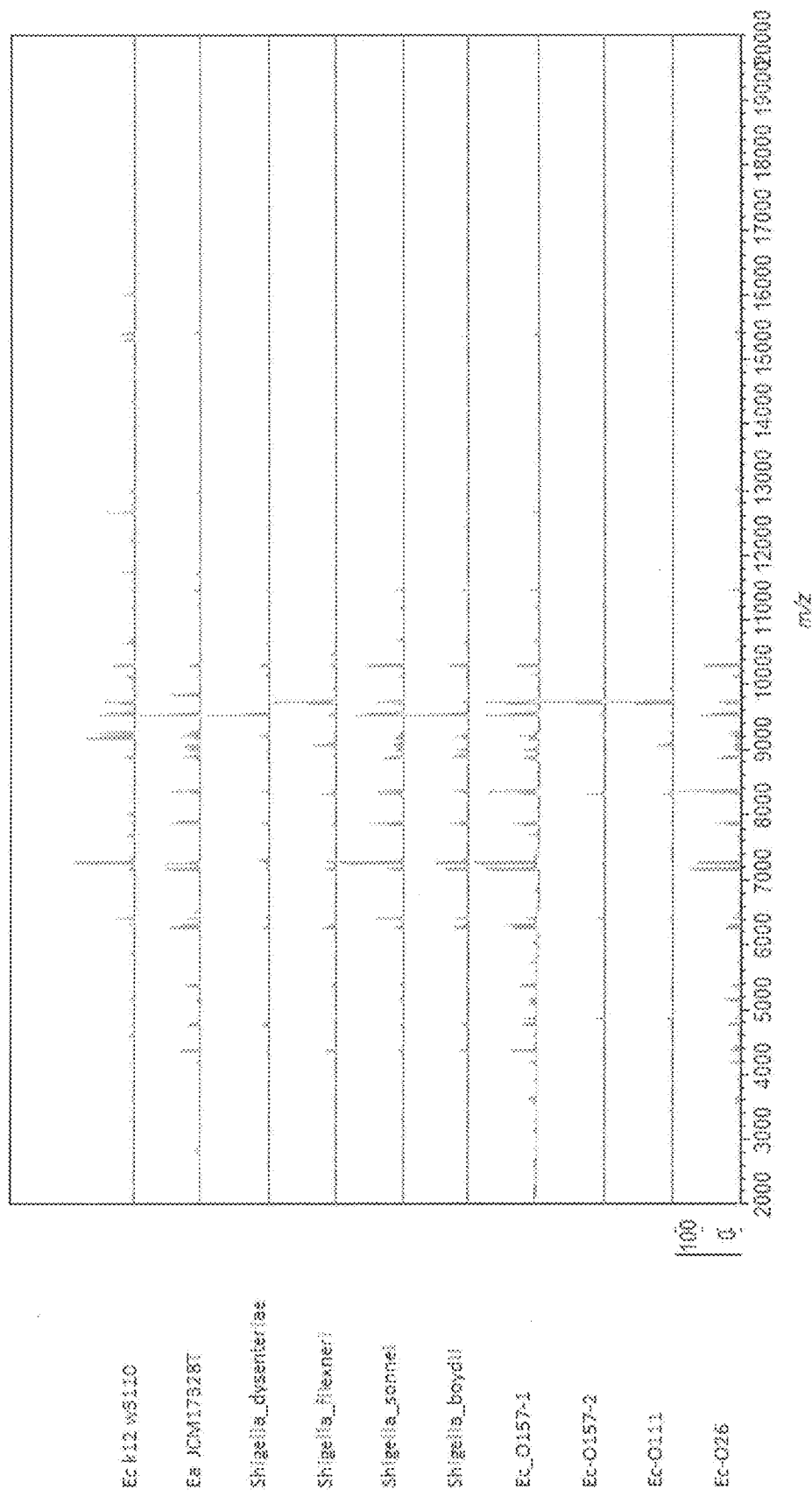
FIG. 9 is a chart obtained by MALDI-TOF-MS.

Hereinafter, a specific embodiment of a method for discriminatinga microorganism according to the present invention will be described.

FIG. 1 is an overall view of a microorganism discrimination system used in the method for discriminating a microorganism according to the present invention. The microorganism discrimination system is roughly made up of a mass spectrometry unit 10 and a microorganism determination unit 20. The mass spectrometry unit 10 includes an ionization unit 11 that ionizes molecules and atoms in a sample by a matrix-assisted laser desorption ionization (MALDI) method and a time-of-flight mass separator (TOF) 12 that separates various ions emitted from the ionization unit 11 in accordance with a mass-to-charge ratio.

The TOF 12 includes an extraction electrode 13 that extracts ions from the ionization unit 11 to guide the ions into an ion flight space in the TOF 12 and a detector 14 that detects ions that are mass-separated in the ion flight space.

The substance of the microorganism determination unit 20 is a computer such as workstation or a personal computer, and a central processing unit (CPU) 21 as a central processing unit, a memory 22, a display unit 23 including a liquid crystal display (LCD), an input unit 24 including a keyboard, a mouse and the like, and a storage unit 30 including a mass storage device such as a hard disk and a solid state drive (SSD) are connected to one another, An operating system (OS) 31, a spectrum creation program 32, a genus/species determination program 33, and a subclass determination program 35 (program according to the present invention) are stored in the storage unit 30 and also, a first database 34 and a second database 36 are stored. The microorganism determination unit 20 further includes an interface (LT) 25 to control direct connection with an external device and connection via a network such as a Local Area Network (LAN) with an external device or the like, and is connected to the mass spectrometry unit 10 from the interface 5 via a network cable NW (or wireless LAN).

In FIG. 1, a spectrum acquisition unit 37, an m/z reading unit 38, a subclass determination unit 39, a cluster analysis unit 40, and a dendrogram (lineage diagram) creation unit 41 are shown as relating to the subclass determination program 35. Basically, these units are functional means implemented with software by the subclass determination program 35 being executed by the CPU 21. The subclass determination program 35 is not necessarily a single program, but may be a function incorporated into portion of a program for controlling the genus/species determination program 33 or the mass spectrometry unit 10, and its form is not particularly limited. As the genus/species determination program 33, for example, a program for performing microorganism identification by a conventional fingerprint method or the like can be used.

Also, in FIG. 1, the spectrum creation program 32, the genus/species determination program 33, the subclass determination program 35, the first database 34, and the second database 36 are mounted on the terminal operated by the user, but at least a portion or all of these units may be provided in another device connected to the terminal via a computer network so that processing by a program and/or access to a database provided in the other device is performed according to instructions from the terminal.

A large number of mass lists related to known microorganisms are registered in the first database 34 of the storage unit 30. These mass lists enumerate the mass-to-charge ratios of ions detected upon mass spectrometry of a certain microbial cell and include, in addition to the information of the mass-to-charge ratios, at least information (classification information) of the classification group to which the microbial cell belongs (family, genus, species, etc.). Such mass lists are desirably created based on data (actual measurement data) obtained through actual mass spectrometry of various microbial cells in advance by an ionization method and mass separation method similar to those of the mass spectrometry unit 10.

When creating a mass list from the actual measurement data, a peak appearing in a predetermined mass-to-charge ratio range is first extracted from the mass spectrum acquired as the actual measurement data. In this case, by setting the mass-to-charge ratio range to about 2,000 to 35,000, protein-derived peaks can be mainly extracted. Also, by extracting only peaks whose peak height (relative intensity) is equal to or greater than a predetermined threshold, undesirable peaks (noise be excluded. Since the ribosomal protein group is expressed in a large amount in the cell, most of the mass-to-charge ratios listed in the mass list can he derived from the ribosomal proteins by setting the threshold appropriately. Then, the mass-to-charge ratios (m/z) of the peaks extracted in the above manner are listed for each cell and registered in the first database 34 after adding the classification information and the like. In order to suppress variations in gene expression due to culture conditions, it is desirable to standardize culture conditions in advance for each microbial cell used for collecting actual measurement data.

Information about marker proteins to discriminate known microorganisms at a level (species, subspecies, pathogenic type, serotype, strain, etc.) lower than the classification level discriminable by the genus/species determination program 33 is registered in the second database 36 of the storage unit 30. Information about the marker protein includes at least information about the mass-to-charge ratio (m/z) of the marker protein in the known microorganism. In the second database 36 according to the present embodiment, as information about marker proteins to determine which bacterial species of *Escherichia coli, Shigella* bacteria, and *E. albertii* the test microorganism contains, mass-to-charge ratio values of at least 7 ribosomal proteins L31, L13, S15, L25, HNS, HdeB, and L29 are stored. These mass-to-charge ratio values of 7 ribosomal proteins will be described below.

The value of the mass-to-charge ratio of the marker proteins stored in the second database 36 is desirably selected by comparing the calculated mass obtained by translating the base sequence of each Immarker protein into an amino acid sequence with the mass-to-charge ratio detected by actual measurement. The base sequence of the marker protein may be, in addition to determination by sequencing, acquired from a public database, for example, a database or the like of National Center for Biotechnology Information (NCBI) and used. When calculating the calculated mass from the amino acid sequence, it is desirable to consider cleavage of the N-terminal methionine residue as a post-translational modification. Specifically, when the penultimate amino acid residue is Gly, Ala, Ser, Pro, Val, Thr, or Cys, the theoretical value is calculated assuming that the N-terminal methionine is cleaved. In addition, molecules added with protons are actually observed by MALDI-TOF MS and thus, it is desirable to determine the calculated mass by adding the protons (that is, the theoretical value of the mass-to-charge ratio of ions obtained when each protein is analyzed by MALDI-TOF MS).

The discrimination procedure of *Escherichia coli. Shigella* bacteria, and *E. albertii* using a microorganism discrimination system according to the present embodiment will be described with reference to the flowchart.

First, the user prepares a sample containing constituent components of a test microorganism and sets the sample to the mass spectrometry unit 10 to perform mass spectrometry. In this case, as the sample, in addition to a cell extract or a cellular component such as a ribosomal protein purified from a cell extract, a bacterial cell or a cell suspension may be used as it is.

The spectrum creation program 32 acquires a detection signal obtained from the detector 14 of the mass spectrometry unit 10 via the interface 25 and creates a mass spectrum of the test microorganism based on the detection signal (step S101).

Next, the species determination program 33 checks the mass spectrum of the test microorganism against a mass list of known microorganisms recorded in the first database 34 and extracts a mass list of known microorganisms having a mass-to-charge ratio pattern similar to the mass spectrum of the test microorganism, for example, a mass list including peaks that coincide with each peak in the mass spectrum of the test microorganism within a predetermined error range (step S102). Subsequently, the species determination program 33 refers to the classification information stored in the first database 34 in association with the mass list extracted in step S102, thereby determining the species to which the known microorganism corresponding to the mass list belongs (step S103), if the species is not any one of *Escherichia coli, Shigella* bacteria, and *E. albertii*) in step S104), the species is output to the display unit 23 as a species of the test microorganism (step S109) before the discrimination processing is terminated. On the other hand, if the species is any one of *Escherichia coli, Shigella* bacteria, and *E. albertii* (Yes in step S104), then the processing proceeds to the discrimination processing by the subclass determination program 35. If it is determined in advance that the sample contains *Escherichia coli, Shigella* bacteria, and *E. albertii* by other methods, the processing may proceed to the subclass determination program 35 without using the species determination program using the mass spectrum.

In the subclass determination program 35, first the subclass determination unit 39 reads the mass-to-charge ratio values of 7 ribosomal proteins L31, L13, S15, L25, HNS, HdeB, and L29 as the marker protein from the second database 36 (step S105). Subsequently, the spectrum acquisition unit 37 acquires the mass spectrum of the test microorganism created in step S101. Then, the m/z reading unit 38 selects peaks appearing in the mass-to-charge ratio range stored in the second database 36 in association with each of the marker proteins on the mass spectrum as peaks corresponding to each of the marker proteins and reads the mass-to-charge ratios of the peaks (step S106). Then, the cluster analysis is performed using the read mass-to-charge ratio as an index. Specifically, the subclass determination unit 39 compares the mass-to-charge ratio with the value of the mass-to-charge ratio of each marker protein read out from the second database 36, and determines the attribution of the protein with respect to the read mass-to-charge ratio (step S107). Then, the cluster analysis is performed based on the determined attribution to determine the species of the test microorganism (step S108), and the determined species is output to the display unit 23 as the discrimination result of the test microorganism (step S109).

In the foregoing, an embodiment to carry out the present invention has been described above with reference to the drawings, but the present invention is not limited to the above embodiment and appropriate modifications are permitted within the scope of the spirit of the present invention.

EXAMPLES (1) Strains Used

*Escherichia coli, Escherichia albertii*, and *Shigella* bacteria available from culture collection institutes of RIKEN BioResource Center, Japan Collection of Microorganisms (JCM, Tsukuba, Japan), National Institute of Technology and Evaluation, Biological Resource Center (NBRC, Kisarazu. Japan) and National BioResource Project GTC Collection (Gifu, Japan) shown in FIG. 3 were used for the analysis.

(2) Analysis of DNA

The DNA sequences of the ribosomal protein genes that may be the S10-spc-alpha operon and biomarkers shown in FIG. 4 were analyzed with a primer designed based on the consensus sequence. More specifically, the genomes were extracted from each strain by a conventional method, and using the genomes as a. template, the target gene region was amplified by PCR using KOD plus. The obtained PCR product was purified and used as a template for sequence analysis. Sequence analysis was performed using Big Dye ver. 3.1 Cycle Sequencing Kit (Applied Biosystems, Foster City, Calif). The DNA sequence of each gene was transformed into the amino acid sequence of each gene, and based on the amino acid mass shown in FIG. 5, a mass-to-charge ratio was calculated and defined as the theoretical mass value.

(3) Analysis by MALDI-TOF MS

Bacterial cells grown in an LB agar medium were used as an analysis sample, and whole-cell analysis was performed. One colony of the analysis sample was added to 10 µL of a sinapinic acid matrix agent (20 mg/mL of sinapinic acid (Wako Pure Chemical Corporation, Osaka, Japan) in a solution of 50 v/v % acetonitrile and 1 v/v % trifluoroacetic acid) and sufficiently stirred, and 1.2 µL of the mixed solution was mounted on a sample plate and allowed to air dry. For the MALDI-TOF MS measurement, an AXIMA microorganism identification system (Shimadzu Corporation, Kyoto, Japan) was used and the sample was measured in the positive linear mode and in the spectral range of 2000 m/z to 35000 m/z. The above calculated mass was matched with the measured mass-to-charge ratio with an allowable error of 500 ppm and appropriately corrected. For the calibration of the mass spectrometer, the *Escherichia coli* DH5α strain was used, and the calibration was performed in accordance with the instruction manual.

(4) Construction of a Database for Discrimination of *Escherichia coli, E. albertii*, and *Shigella* Bacteria The theoretical mass value of the ribosomal protein obtained in above (2) was checked against the peak chart by MALDI-TOFMS obtained in (3), and regarding the proteins that could be detected by actual measurement, it was confirmed that there was no difference between the theoretical mass value calculated from the gene sequence and the actual measurement value. Then, the theoretical mass values and the actual measurement values of ribosomal proteins in the S10-spc-α operon and proteins that may be other biomarkers showing different masses depending on strains were summarized in FIG. 6A as a database. In FIG. 6, numerals in the left column of each ribosomal protein represent the theoretical mass of the mass-to-charge ratio (m/z) calculated from each gene and numerals in the right column represent the attribution number. FIG. 6B shows the relationship between the mass-to-charge ratio of each ribosomal protein and the attribution number shown in FIG. 6A. Symbols of "○" and "Δ" in the bottom column of each ribosomal protein represent the mass peak detection result by actual measurement. The symbol of "○" means that the peak was detected as a peak within the range of 500 ppm of the theoretical value in the default peak processing setting (threshold offset: 0.015 mV, threshold response: 1.200) of the AMNIA microorganism identification system. The symbol of "Δ" means that the theoretical value mass difference in each strain or the difference from the peak of other ribosomal proteins was within 500 ppm respectively and that the peak was detected but the mass difference could not be discriminated.

As can be seen from these figures, the ribosomal proteins S5, L15, S13, and L29 encoded in the S10-spc-alpha operon, L31, L22, L19, L20, and L13 outside the operon, and S15, L25, HNS, and HdeB shown in Patent Literature 3 (a total of 13 type) have different theoretical mass values depending on *Escherichia coli, Escherichia albertii*, and *Shigella* bacteria strain, suggesting the possibility that these ribosomal proteins may he useful protein markers that can be used for discrimination.

However, it seems that S5, L15, S13, L22, L19, and L20 may be important biomarkers for discrimination of strains having a theoretical mass difference of 500 ppm or more, but these ribosomal proteins could not be detected by actual measurement, and thus these ribosomal proteins were considered not suitable as biomarkers.

On the other hand, a total of 7 proteins L31, L29, L13, HdeB, S15, L25, and HNS were detected in a stable manner regardless of strains and had a mass difference depending on strains of 500 ppm or more, and thus it was found that these proteins are useful as biomarkers for discrimination of *Escherichia coli, Escherichia albertii*, and *Shigella* bacteria in MALDI-TOF MS. Therefore, these 7 ribosomal proteins were used as biomarkers in the following experiments.

(5) Attribution of MALDI-TOFMS Actual Measurement Values by Software

The theoretical mass values of the above 7 proteins L31, L29, L13, HdeB, S15, L25, and HNS were registered in software as shown in Patent Literature 2. Regarding L29, there was a strain having an interfering peak at the position of m/z 7274, and thus only 3 peaks of m/z 7261.45, m/z 7302.5, and m/z 7288.47 were registered as biomarker peaks.

Next, actual measurement data in MALDI-TOF MS were analyzed by this software to examine whether each biomarker was correctly attributed as the registered mass peak. As a result, as shown in FIG. 7A, all hiomarker mass peaks of all strains were attributed as the registered mass number. FIG. 7B shows the relationship of the mass-to-charge ratio of each ribosomal protein and the attribution nwnber shown in FIG. 7A. When the serotype of each strain was checked, each type strain of *Escherichia albertii, Shigella dysenteriae, Shigella flexneri, Shigella sonnei*, and *Shigella boydii* could be discriminated from *Escherichia coli* K12 strain, O157 strain, O26 strain and O111 strain.

From these results, it was found that using the masses of L31, L29, L13, HdeB, S15, L25, and HNS as biomarkers in the MALDI-TOF MS analysis is useful for discrimination of *Escherichia coli, Escherichia albertii*, and *Shigella* bacteria.

Regarding the biomarkers found this time, unlike the mass peaks [m/z] 2400, 3792, 4162, 4856, 5096, 5752, 7288, 7302, 8323, 8455, 9711, 9736, and 10458 reported in Non Patent Literature 15, correct masses were calculated from the gene information and checked against the actual measurement values. As a result, it became possible to provide a mass database with high reliability for the first time.

(6) Gene Sequence and Amino Acid Sequence of a Biomarker

The DNA sequence and the amino acid sequence in each strain of proteins L31, L29, L13, HdeB, S15, L25, and HNS that are encoded in and outside the S10-spc-alpha operon, which show different theoretical mass values depending on strains of *Escherichia coli*, *Escherichia albertii*, and *Shigella* bacteria, are summarized in FIG. 14A to FIG. 14F and FIG. 15A to FIG. 15B.

(7) Actual Measurement of *Escherichia coli*, *Escherichia albertii*, *Shigella dysenteriae*, *Shigella flexneri*, *Shigella sonnei*, and *Shigella boydii*

The discrimination result by the existing fingerprint method (SARAMIS) was compared with the discrimination result using the theoretical mass value of each biomarker shown in FIG. 8B as an index. First, in actual measurement in MALDI-TOF MS, a chart as shown in FIG. 9 was obtained. This result was analyzed by SARAMIS in accordance with the instruction manual of the AXIMA microorganism identification system. The obtained result is shown in FIG. 10. As can be seen from FIG. 10, *Escherichia coli* was identified as "*Escherichia coli*" with a discrimination rate of 90% or more. However, all of *Escherichia albertii*, *Shigella dyseteriae*, *Shigella flexneri*, *Shigella sonnei*, and *Shigella boydii* were misidentified as "*Escherichia coli*" with a discrimination rate of 89 to 99%.

Figure 11B:
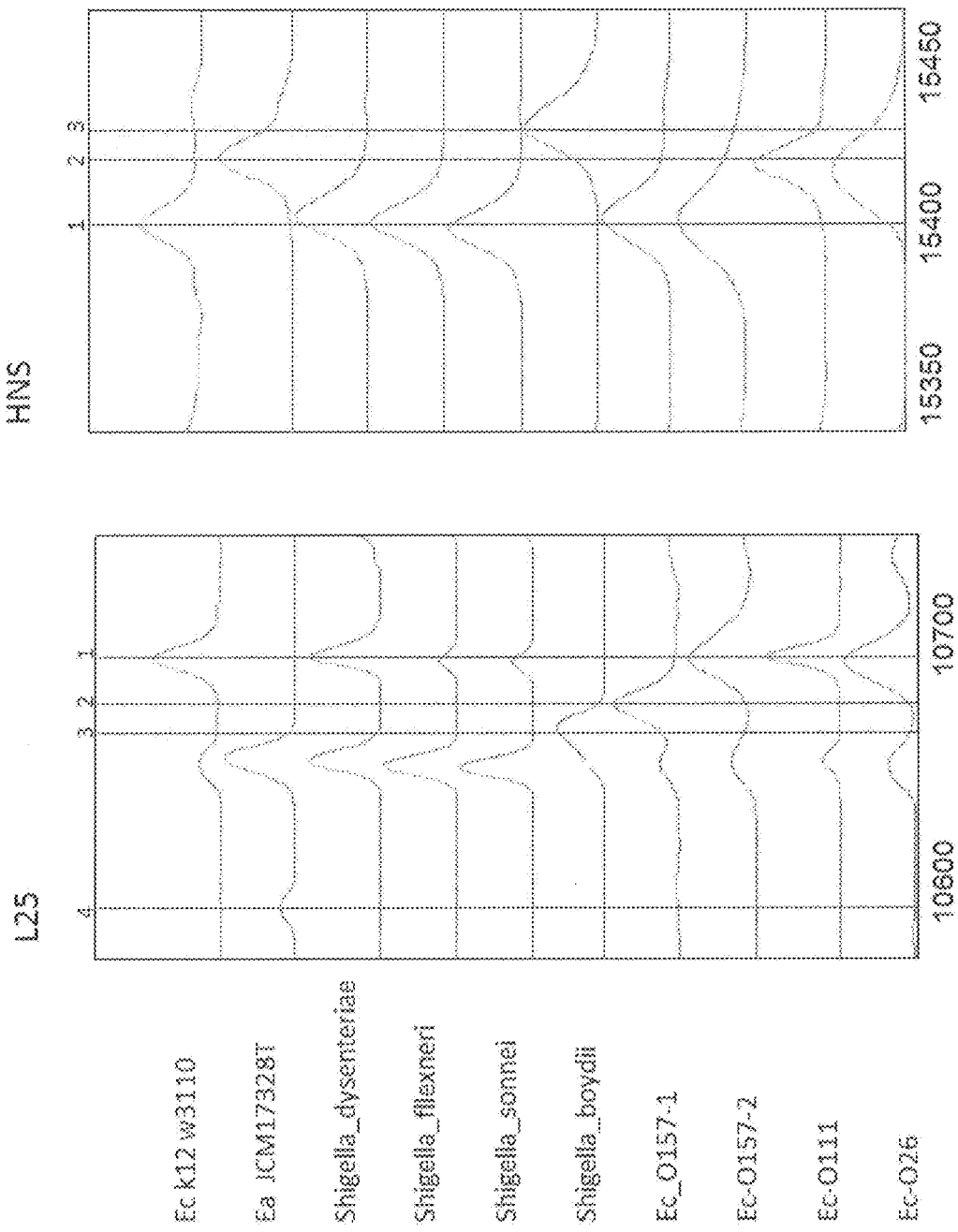
FIG. 11B is a peak chart obtained by MALDI-TOF MS measurement (part 2).

Hence, it was attempted to discriminate the actual measurement results of these strains based on the theoretical mass database shown in FIG. 8B. Regarding m/z 7274.44 of L29, an interfering peak appears at near m/z 7274.44 for strains having different theoretical masses, and thus peaks other than this of m/z 7261.45, m/z 7302.497, and m/z 7288.471 were used as biomarker peaks. FIG. 11A to FIG. 11C are enlarged views of the biomarker peak of the chart of FIG. 9. As can be seen from these Figures, the mass-to-charge ratio of each biomarker was shifted and peaks can be distinguished. When the actual measurement values of these 7 biomarkers were compared with the theoretical values and attributed, the results shown in FIG. 8A were obtained. The relationship between the attribution number shown in FIG. 8A and the theoretical value is as shown in FIG. 8B.

Figure 12:
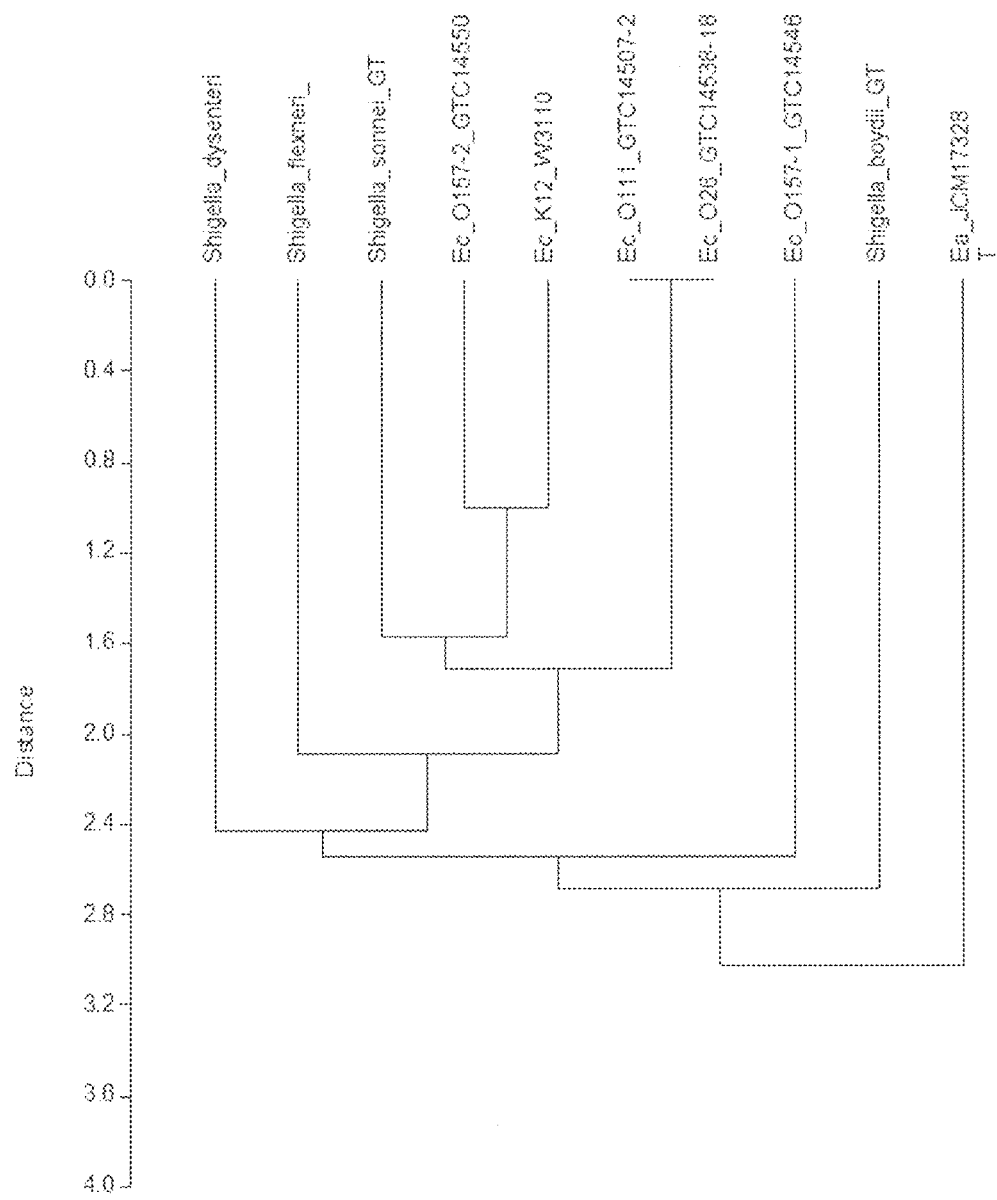
FIG. 12 is a dendrogram created using 7 ribosomal proteins.
Figure 13:
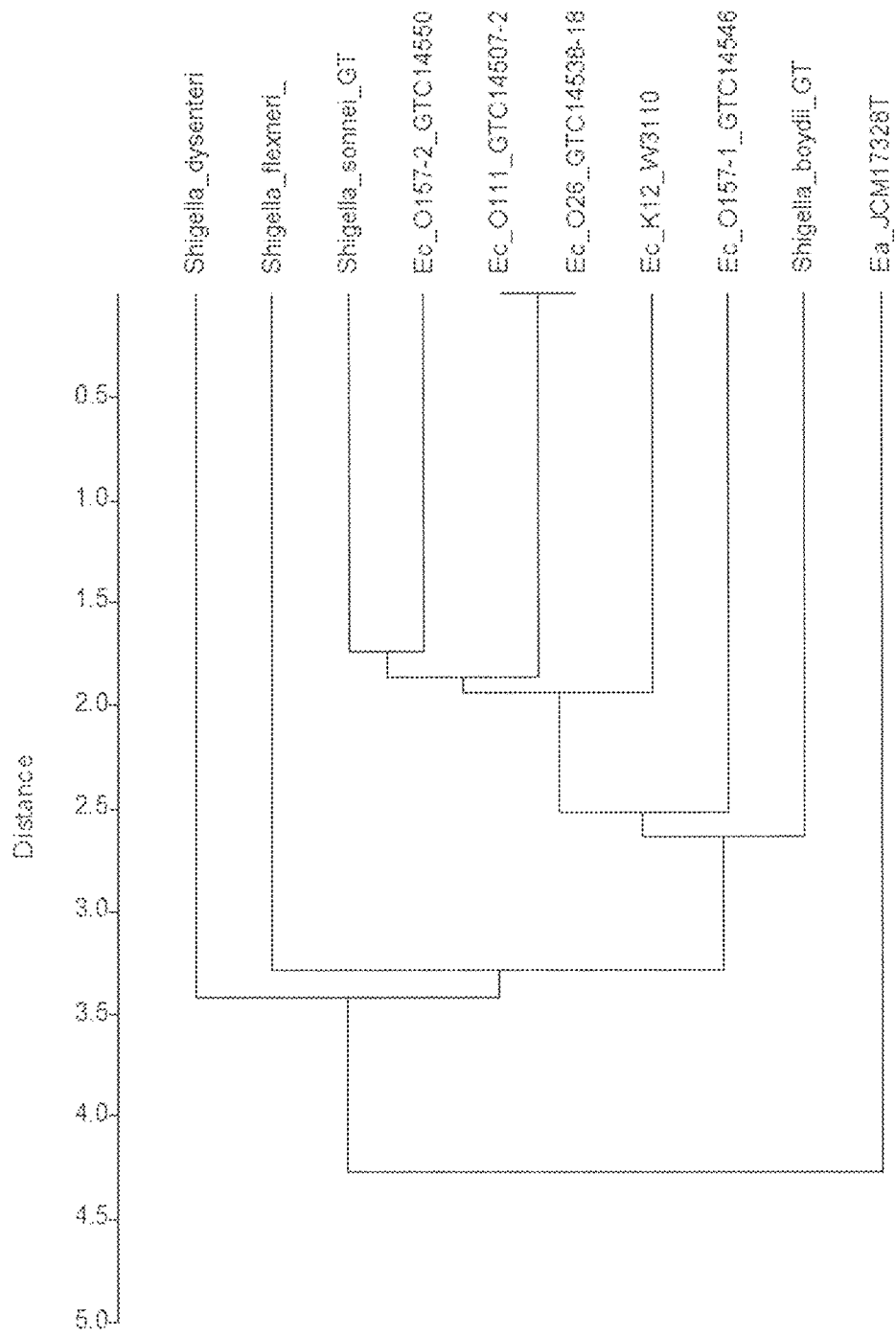
FIG. 13 is a dendrogram created using 13 ribosomal proteins.

A lineage diagram drawn using the attribution results of 7 biomarkers is shown in FIG. 12. Also, a lineage diagram drawn using the attribution results of 13 biomarkers (FIG. 7A) is shown in FIG. 13. It can be seen that species can be discriminated in both lineage diagrams. From these results, the discrimination method using the mass difference of biomarkers found in the present invention is a very effective method.

REFERENCE SIGNS LIST

10 . . . Mass Spectrometry Unit
11 . . . Ionization Unit
12 . . . TOF
13 . . . Extraction Electrode
14 . . . Detector
20 . . . Microorganism Determination Unit
21 . . . CPU
22 . . . Memory
23 . . . Display Unit
24 . . . Input Unit
25 . . . I/F
30 . . . Storage Unit
31 . . . OS
32 Spectrum Creation Program
33 . . . Genus/Species Determination Program
34 . . . First Database
35 . . . Subclass Determination Program
36 . . . Second Database
37 . . . Spectrum Acquisition Unit
38 . . . m/z Reading Unit
39 . . . Subclass Determination Unit
40 . . . Cluster Analysis Unit
41 . . . Dendrogram Creation Unit

The invention claimed is:

1. A method for discriminating a microorganism, the method comprising:
   a) a step of subjecting a sample containing a microorganism to mass spectrometry to obtain a mass spectrum;
   b) a reading step of reading a mass-to-charge ratio m/z of a peak derived from a marker protein from the mass spectrum; and
   c) a discrimination step of discriminating which bacterial species of *Escherichia coli*, *Shigella* bacteria, and *Escherichia albertii* is contained in the sample based on the mass-to-charge ratio m/z,
   wherein
   at least one of 13 ribosomal proteins S5, L15, S13, L31, L22, L19, L20, L13, S15, L25, HNS, HdeB, and L29 is used as the marker protein, and
   the *Shigella* bacteria is discriminated based on the mass-to-charge ratio m/z of at least one of ribosomal proteins L29 and L13 and ribosomal proteins L31 and L13.

2. A method for discriminating a microorganism, the method comprising:
   a) a step of subjecting a sample containing a microorganism to mass spectrometry to obtain a mass spectrum;
   b) a reading step of reading a mass-to-charge ratio m/z of a peak derived from a marker protein from the mass spectrum; and
   c) a discrimination step of discriminating which bacterial species of *Escherichia coli*, *Shigella* bacteria, and *Escherichia albertii* is contained in the sample based on the mass-to-charge ratio m/z,
   wherein
   at least one of 13 ribosomal proteins S5, L15, S13, L31, L22, L19, L20, L13, S15, L25, HNS, HdeB, and L29 is used as the marker protein, and
   *Shigella flexneri* of the *Shigella* bacteria is discriminated based on the mass-to-charge ratio m/z of at least one of ribosomal proteins L31 and L29.

3. A method for discriminating a microorganism, the method comprising:
   a) a step of subjecting a sample containing a microorganism to mass spectrometry to obtain a mass spectrum;
   b) a reading step of reading a mass-to-charge ratio m/z of a peak derived from a marker protein from the mass spectrum; and
   c) a discrimination step of discriminating which bacterial species of *Escherichia coli*, *Shigella* bacteria, and *Escherichia albertii* is contained in the sample based on the mass-to-charge ratio m/z,
   wherein
   at least one of 13 ribosomal proteins S5, L15, S13, L31, L22, L19, L20, L13, S15, L25, HNS, HdeB, and L29 is used as the marker protein, and
   *Shigella sonnei* of the *Shigella* bacteria is discriminated based on the mass-to-charge ratio m/z of at least a ribosomal protein L13.

4. A method for discriminating a microorganism, the method comprising:
- a) a step of subjecting a sample containing a microorganism to mass spectrometry to obtain a mass spectrum;
- b) a reading step of reading a mass-to-charge ratio m/z of a peak derived from a marker protein from the mass spectrum; and
- c) a discrimination step of discriminating which bacterial species of *Escherichia coli, Shigella* bacteria, and *Escherichia albertii* is contained in the sample based on the mass-to-charge ratio m/z, wherein at least one of 13 ribosomal proteins S5, L15, S13, L31, L22, L19, L20, L13, S15, L25, HNS, HdeB, and L29 is used as the marker protein, and

*Shigella boydii* of the *Shigella* bacteria is discriminated based on the mass-to-charge ratio m/z of at least one of ribosomal proteins L25, HNS, and L13.

\* \* \* \* \*